United States Patent
So et al.

(10) Patent No.: US 7,372,985 B2
(45) Date of Patent: May 13, 2008

(54) SYSTEMS AND METHODS FOR VOLUMETRIC TISSUE SCANNING MICROSCOPY

(75) Inventors: Peter So, Cambridge, MA (US); Bevin Engelward, Jamacia Plain, MA (US); Timothy Ragan, Cambridge, MA (US); Karsten Bahlmann, Cambridge, MA (US); Ki Hean Kim, Cambridge, MA (US); Lily Hsu, Arlington, MA (US); Hayden Huang, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 717 days.

(21) Appl. No.: 10/642,447

(22) Filed: Aug. 15, 2003

(65) Prior Publication Data

US 2005/0036667 A1 Feb. 17, 2005

(51) Int. Cl.
*G06K 9/00* (2006.01)
(52) U.S. Cl. .................... 382/133; 382/154
(58) Field of Classification Search ........... 382/128, 382/133, 134, 154; 356/39
See application file for complete search history.

(56) References Cited

U.S. PATENT DOCUMENTS

| | | | |
|---|---|---|---|
| 4,960,330 A | 10/1990 | Kerschmann | 356/36 |
| 5,139,338 A | 8/1992 | Pomerantz et al. | 356/376 |
| 5,283,433 A | 2/1994 | Tsien | 250/234 |
| 5,523,543 A | 6/1996 | Hunter, Jr. et al. | 219/121.62 |
| 5,804,813 A | 9/1998 | Wang et al. | 250/201.3 |
| 6,366,357 B1 | 4/2002 | Svetkoff et al. | 356/602 |
| 6,423,960 B1 | 7/2002 | Engelhardt et al. | 250/214 R |
| 6,438,261 B1 * | 8/2002 | Moshe et al. | 382/133 |
| 6,496,267 B1 | 12/2002 | Takaoka | 356/497 |
| 6,684,092 B2 * | 1/2004 | Zavislan | 600/407 |

(Continued)

FOREIGN PATENT DOCUMENTS

DE 196 32 637 A1 2/1998

(Continued)

OTHER PUBLICATIONS

Diaspro, Alberto, et al., "Adapting a Compact Confocal Microscope System to a Two-Photon Excitation Fluorescence Imaging Architecture," Microscopy Research and Technique, 47:196-205 (1999).

(Continued)

*Primary Examiner*—Andrew W. Johns
(74) *Attorney, Agent, or Firm*—Weingarten, Schurgin, Gagnebin & Lebovici LLP

(57) ABSTRACT

In accordance with preferred embodiments of the present invention, a method for imaging tissue, for example, includes the steps of mounting the tissue on a computer controlled stage of a microscope, determining volumetric imaging parameters, directing at least two photons into a region of interest, scanning the region of interest across a portion of the tissue, imaging a plurality of layers of the tissue in a plurality of volumes of the tissue in the region of interest, sectioning the portion of the tissue and imaging a second plurality of layers of the tissue in a second plurality of volumes of the tissue in the region of interest, detecting a fluorescence image of the tissue due to said excitation light; and processing three-dimensional data that is collected to create a three-dimensional image of the region of interest.

27 Claims, 18 Drawing Sheets

U.S. PATENT DOCUMENTS

| | | | |
|---|---|---|---|
| 7,003,143 B1* | 2/2006 | Hewitt et al. | 382/128 |
| 7,110,118 B2 | 9/2006 | Ünlü et al. | 356/450 |
| 7,139,415 B2 | 11/2006 | Finkbeiner | 382/128 |
| 7,194,124 B2* | 3/2007 | Soll et al. | 382/133 |
| 7,197,193 B2 | 3/2007 | Li et al. | 382/285 |
| 7,215,469 B2 | 5/2007 | Nakata et al. | 359/386 |
| 7,274,446 B2 | 9/2007 | Wolleschensky et al. | 356/300 |
| 2001/0052257 A1 | 12/2001 | Magerle | 73/105 |
| 2004/0076315 A1* | 4/2004 | Scoll et al. | 382/128 |
| 2004/0125372 A1 | 7/2004 | Walla et al. | 356/318 |
| 2004/0167806 A1* | 8/2004 | Eichhorn et al. | 705/3 |

FOREIGN PATENT DOCUMENTS

| | | |
|---|---|---|
| DE | 198 19 144 C1 | 6/2000 |
| EP | 0 209 369 A2 | 1/1987 |
| JP | 2000-155097 A | 6/2000 |
| WO | WO 98/02851 A1 | 1/1998 |
| WO | WO 01/14853 A1 | 3/2001 |

OTHER PUBLICATIONS

Hegedüs, Csaba, et al., "3D Reconstruction Based on Hard Tissue Microtome Cross-Section Pictures in Dentistry," Computer Methods and Programs in Biomedicine, 63:77-84 (2000).

Kim, K. H., et al., "Three-Dimensional Image Cytometer Based on a High-Speed Two-Photon Scanning Microscope," Proc. SPIE vol. 4262, p. 238-246, Multiphoton Microscopy in the Biomedical Sciences, Ammasi Periasamy; Peter T. So; Eds., Apr. 2001.

Kim, Ki Hean, et al., "High-Speed, Two-Photon Scanning Microscope," Applied Optics, 38(2): 6004-6009 (Oct. 1, 1999).

Periasamy, Ammasi, et al., "An Evaluation of Two-Photon Excitation Versus Confocal and Digital Deconvolution Fluorescence Microscopy Imaging in Xenopus Morphogenesis," Microscopy Research and Technique, 47:172-181 (1999).

Rademann, Jörg, et al., "Spatially Resolved Single Bead Analysis: Homogeneity, Diffusion, and Adsorption in Cross-Linked Polystyrene," Chem Eur. J., 7(18):3884-3889 (2001).

Shelden, E., and Knecht, D.A., "Reconstruction and Display of Curvilenear Objects From Optical Section Data Using 3-D Curve Fitting Algorithms," Journal of Microscopy, 191(1):97-107 (Jul. 1998).

So, Peter T.C., et al., "Two-Photon Exitation Fluorescence Microscopy," Annu. Rev. Biomed. Eng., 02:399-429 (2000).

Bird et al., Two-photon fluorescence endoscopy with a micro-optic scanning head, Optical Society America, 2003, vol. 28, No. 17, pp. 1552-1554.

Sacconi et al., Multiphoton multifocal microscopy exploiting a diffractive optical element, Optical Society America, 2003, vol. 28, No. 20, pp. 1918-1920.

Jung et al., Multiphoton endoscopy, Optical Society America, 2003, vol. 28, No. 11, pp. 902-904.

Bird et al., Fibre-optic two-photon scanning fluorescence microscopy, The Royal Microscopical Society, Journal of Microscopy, Oct. 2002, vol. 208, Pt 1, pp. 35-48.

Helmchen et al, Enchanced two-photon excitation through optical fiber by single-mode propagation in a large core, Optical Society America, May 20, 2002, vol. 41, No. 15, pp. 2930-2934.

Andersen et al., Time multiplexed multifocal multiphoton microscope, Optical Society America, Optic Letters, 2001, vol. 26, No. 2, pp. 75-77.

Helmchen et al. A miniature head-mounted two-photon microscope: high-resolution brain imaging in freely moving animals, Neuron, 2001, Cell Press, vol. 31, pp. 903-912.

Nielsen et al., High efficiency beam splitter for multifocal multiphoton microscopy, The Royal Microscopical Society, Journal of Microscopy, 2001, vol. 201, Pt 3, pp. 368-376.

Bewersdorf et al, Multifocal multiphoton microscopy, Optical Society America, Optical Letters, 1998, vol. 23, No. 9, pp. 655-657.

Buist et al., Real time two-photon absorption microscopy using multipoint excitation, The Royal Microscopical Society, Journal of Microscopy, 1998, vol. 192, Pt 2, pp. 217-226.

Denk et al., Two-photon laser scanning fluorescence microscopy, School of Applied and Engineering Physics, Dept. of Physics, Cornell University, Ithaca NY 14853.

Webb et al., A wide-field time-domain fluorescence lifetime imaging microscope with optical sectioning, American Institute of Physics, Review of Scientific Instruments, 2002, vol. 73, No. 4, pp. 1898-1907.

Leveque-Fort et al., Time-resolved multifocal multiphoton microscopy, Biomedical Optics, SPIE, 2003, vol. 5139, pp. 173-179.

Kim et al., Usage of multi anode PMT on the multi-photon fluorescence spectroscopy and video rate microscopy, IEEE, 2002.

* cited by examiner

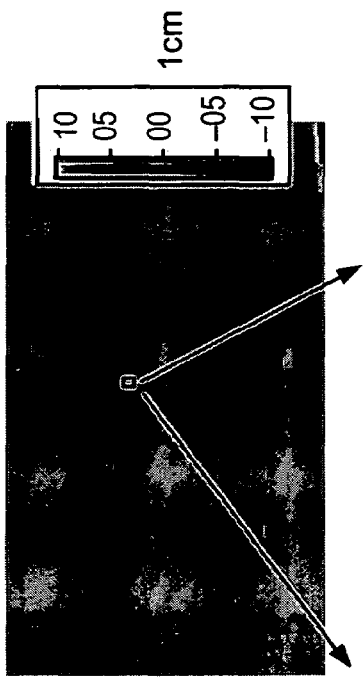
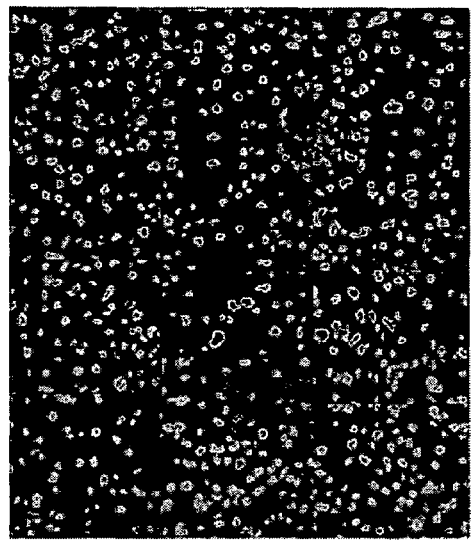
Image Cytometry Data
Fluorescence ratio image of a mixture of 3T3 cells and YFP cells dispersed on a coverslip. The cell nuclei are stained with Hoechst 3342
Figure 8A
Figure 8B
Figure 8C

High Resolution Volumetric Imaging of Mouse Brain

A mouse was genetically engineered to co-express GFP along with actin in the brain. The brain was excised and then fixed in 4% paraformaldehyde and then embedded in paraffin.

Imaging Parameters:
1 μm xy resolution; 3 μm z resolution
Eighteen 60 μm microtome sections
Imaging Time: 45 minutes
Approximately 1*10⁵ cells A cell layer in the epidermis Basal cell layer in epidermis Collagen/elastin fibers in the dermal layer Honeycomb-like cartilage structure

SYSTEMS AND METHODS FOR VOLUMETRIC TISSUE SCANNING MICROSCOPY

GOVERNMENT SUPPORT

This invention was supported, in whole or in part, by a grant R2I/33 CA84740 from the National Institute of Health. The Government has certain rights in the invention.

BACKGROUND OF THE INVENTION

The development of new tools and techniques to investigate cell behavior is vital to the understanding of basic biology and the development of new pharmaceuticals and clinical treatment techniques. Techniques such as flow cytometry and image cytometry have allowed researchers and clinicians to assay populations of cells on the order of $10^5$ to $10^8$ and to categorize these into subpopulations and identify rare events on the order of 1 in $10^6$.

Cytometry is an analytical method capable of precisely quantifying the functional states of individual cells by measuring their optical characteristics based on fluorescence or scattered light. As a quantitative analytical method applicable to individual cells, it has contributed to the progress of cell biology and is now widely used in the basic and clinical study. Cytometry can be classified into two categories, flow cytometry and image cytometry, based on the measurement method. Flow cytometry monitors the properties of cells carried through the detection area in a fluid stream. It has several unique advantages. The most important one is the rapidity of this measurement scheme. With throughput rate up to 100,000 cells per second, the analysis of a large cell population for the detection of a few rare cells, are possible. Also, based on multi-parametric analysis, it is well suited to identify and distinguish the properties of cell sub-populations. Further, cell sorting methods implemented with flow cytometry enables physical selection of a specific cellular sub-population for further analysis and clonal propagation. Therefore, flow cytometry/cell sorting methods are now an indispensable tool in immunology, molecular and cell biology, cytogenetics, and the human genome project.

Image cytometry has been recently introduced as a complementary method for flow cytometry. This method images individual cells plated in a 2-D culture plate. Cellular morphology and biochemical states are typically quantified by fluorescence microscopy. Although the throughput rate of this method is relatively low (approximately 200 cells per second), it has several unique advantages. Individual cells of interest can be re-located so that they can be further analyzed. One key example is the ability of this method to monitor the temporal evolution of a cellular sub-population. Image cytometry also provides cellular structural information, such as the relative distribution of a fluorochrome in the nucleus and in the cytoplasm with micron level resolution.

Two-photon fluorescence microscopy (TPM) is important for biological imaging. This technology enables noninvasive study of biological specimens in three dimensions with submicrometer resolution. Two-photon excitation of fluorophores results from the simultaneous absorption of two photons. This excitation process has a number of unique advantages, such as reduced specimen photodamage and enhanced penetration depth. It also produces higher-contrast images and is a novel method to trigger localized photochemical reactions.

Two-photon microscopy continues to find an increasing number of applications in biology and medicine. In neurobiology studies, TPM has been applied to study the neuron structure and function in intact brain slices, the role of calcium signaling in dendritic spine function, neuronal plasticity and the associating cellular morphological changes, and hemodynamics in rat neocortex. In embryology studies, two-photon imaging has been used to examine, for example, calcium passage during sperm-egg fusion, the origin of bilateral axis in sea urchin embryos, cell fusion events in C. elegans hypodermis, and hamster embryo development.

Further experiments in TPM tissue imaging include the imaging of the relative transparent ex vivo rabbit cornea based on reduced pyridine nucleotides, NAD(P)H. The methods to image more opaque tissues such as skin and intestine are also being refined.

Two-photon microscopy is an important tool for noninvasive biomedical diagnosis. Two-photon excitation is a fluorescence technique providing an opportunity to assess tissue biochemistry and structures down to the depth of several hundred micrometers. Although the clinical potentials of two-photon microscopy have been demonstrated, significant engineering challenges remain in terms of adapting this technology to the clinical setting.

There still remains a need for imaging of thick samples whose axial dimensions extend beyond the practical working depth of a microscope objective. A further obstacle in implementing this technology is speed. Using a traditional confocal microscope, imaging a one $cm^3$ specimen may require upwards of weeks. The slow data acquisition speed makes imaging large specimens in extended depth impractical.

SUMMARY OF THE INVENTION

The systems and methods of the present invention include imaging techniques that provide quantification of morphological, biochemical and/or genetic states of cells inside tissues. Preferred embodiments of the present invention include a high-speed, two-photon, or multi-photon scanning microscope used, for example, for deep tissue imaging in highly scattering media with minimal photodamage. Real-time tissue images with submicrometer resolution in three- or two-dimensions can be obtained. A main advantage of two-photon video-rate imaging lies with its low phototoxicity. The short, pixel dwell time due to high scanning speed involves the need for optimization of the light budget.

Another preferred embodiment improves on the excitation efficiency and includes compressing the laser pulse width by means of group velocity compensation and increasing the pulse repetition rate to approximate the inverse of typical fluorescence decay lifetimes. High-speed, three-dimensional (3-D) resolved two-photon microscopy provides new opportunities for the development of noninvasive biomedical applications, including optical biopsy, quantitative study of 3-D tissue architecture, and monitoring of wound healing and tissue regeneration.

A method for imaging tissue, for example, includes the steps of mounting the tissue on a computer controlled stage of a microscope, determining volumetric imaging parameters, directing at least two photons into a region of interest, scanning the region of interest across a portion of the tissue, imaging a plurality of layers of the tissue in a plurality of volumes of the tissue in the region of interest, sectioning the portion of the tissue and imaging a second plurality of layers of the tissue in a second plurality of volumes of the tissue in the region of interest, detecting a fluorescence image of the tissue due to said excitation light; and processing three-dimensional data that is collected to create a three-dimensional image of the region of interest.

The method includes a multi-photon microscope. The penetration depth of the multi-photon microscope is in the range of approximately 200-500 µm. The step of sectioning further includes a microtome system integral with the microscope. The speed of the step of imaging includes at least 5 frames per second. The step of scanning further includes video rate scanning (approximately 30 frames per second). The method further includes providing a depth resolution of approximately 0.1 µm or higher. In a preferred embodiment the depth resolution is between a range of 0.1 and 2 µm.

In accordance with another aspect of the invention, a system for providing a three-dimensional image of a region of interest, includes a light source for producing excitation light and providing at least two photons into a region of interest, a scanning microscope optically coupled to the light source, a tissue sectioning device such as, for example, but not limited to, a rotating blade, vibratome or microtome mechanically coupled to the microscope, an x-y scanner to scan the region of interest, an image sensor that detects a plurality of images of the region of interest; and a data processor that processes the plurality of images to produce a processed three-dimensional image of the region of interest.

The system can include a multi-photon microscope. The microscope can be a confocal microscope. The light source is preferably a Titanium-Sapphire laser or a picosecond or femtosecond laser. The system can include a rotating polygonal mirror that provides a fast scanning axis and a galvanometer driven mirror that provides a slow scanning axis and. The system also includes a piezoelectric-driven lens translator that provides a depth axis. The system has at least one diode to generate a reference signal. The image sensor can be a charge coupled device (CCD), an avalanche photodiode or a photomultiplier tube (PMT). The excitation light is in the range of 650-1200 nm and preferably in the range of 700-1100 nm for two photon excitation.

In another embodiment, a method of imaging tissue, includes the steps of mounting the tissue in a multi-photon microscope, directing at least two photons onto a region of interest, scanning a plurality of layers of the tissue in the region of interest and to limit the region of excitation, imaging a plurality of layers in the region of interest in the tissue, detecting a fluorescence image of the tissue due to said excitation light in the region of interest, processing the detected fluorescence image including the steps of sequentially storing a plurality of portions of a three-dimensional image data set, enhancing the image data set, registering individual three-dimensional data sets to generate a large three-dimensional data set, and displaying the three-dimensional data set of the region of interest.

The step of processing can further include compressing the three-dimensional data set, identifying and quantifying features of the region of interest. The step of processing further includes analyzing the three-dimensional data set. The step of imaging includes, for example, imaging mitotic recombination in tissues in transgenic animals wherein recombination events give rise to a fluorescent signal.

In accordance with another aspect of the present invention, a method of imaging tissue includes initially scanning a plurality of layers of tissue at a lower resolution, optically or spectrally or using a combination of both, followed by imaging a certain identified region of interest using a higher resolution imaging mode as described herein before.

The foregoing and other features and advantages of the systems and methods for volumetric tissue scanning microscopy will be apparent from the following more particular description of preferred embodiments of the system and method as illustrated in the accompanying drawings in which like reference characters refer to the same parts throughout the different views. The drawings are not necessarily to scale, emphasis instead being placed upon illustrating the principles of the invention.

BRIEF DESCRIPTION OF THE DRAWINGS

FIGS. 8A-8C are fluorescence ratio images and related images of subregions, respectively, in accordance with a preferred embodiment of the present invention.

FIGS. 11A-11D are three-dimensional reconstructed two-photon images of dermal and subcutaneous structures of a mouse ear tissue specimen, wherein FIG. 11A illustrates epidermal keratinocytes, FIG. 1B illustrates basal cells, FIG. 11C, collagen/elastin fibers and FIG. 11D cartilage structure in accordance with a preferred embodiment of the present invention.

FIGS. 14A-14C are Zemax simulations of an MMM incorporating an 8×8 micro lens array wherein FIG. 14A is a surface plot of the Huygens point spread functions of the foci produced by the 8×8 in an MMM and a 1.2 NA water immersion objective lens, FIG. 14B is a spot diagram of the 64 foci spanning a linear dimension of 200 µm and FIG. 14C is an intensity plot of the Huygens point spread function in the x/y plane, produced by the center microlens, respectively, in accordance with a preferred embodiment of the present invention.

DETAILED DESCRIPTION OF THE INVENTION

Figure 1A:
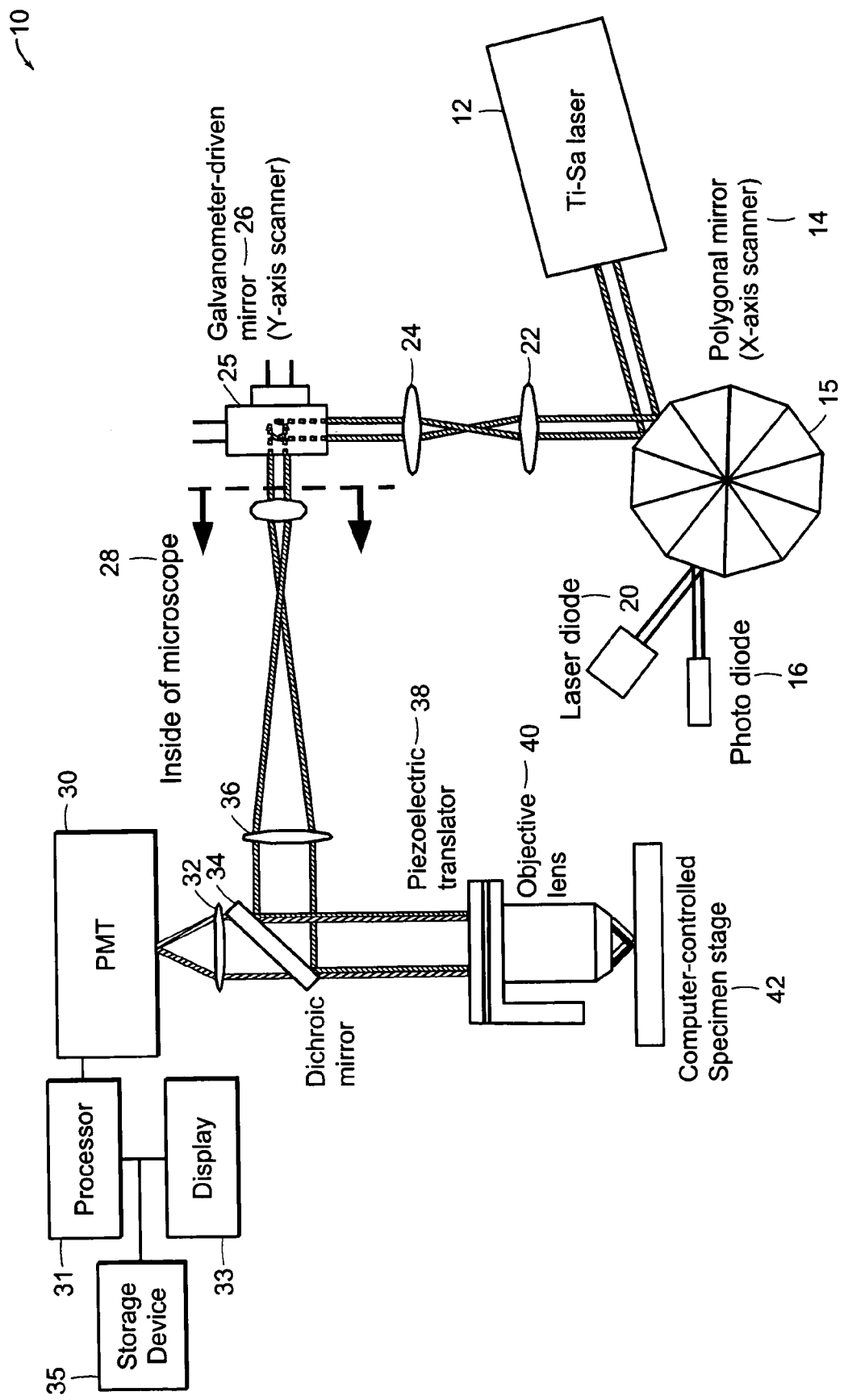
FIGS. 1A and 1B are schematic views of a video-rate, two-photon microscopy system in accordance with a preferred embodiment of the present invention, with a photomultiplier tube (PMT) and a charge coupled device (CCD), respectively.

The systems of the preferred embodiment include an image cytometry method that provides statistically accurate quantification of morphological, biochemical and/or genetic states of cells inside three-dimensional tissues in situ. A high throughput multi-photon microscope is utilized for its penetration depth, which is on the order of 200-500 µm in typical tissues. An automatic microtome system enables analysis of even thicker specimens by serially removing tissue layers after they have been imaged. This system is important in areas such as, for example, but not limited to, pharmacology, toxicology and cancer biology.

A preferred embodiment of the system includes high-speed, over 5 frames per second, multi-foci multiphoton microscope based on low cost, high sensitivity multi-anode photomultiplier tube detectors. Two or more detection channels are integrated into the emission light path to enable spectrally resolved diagnosis. The embodiment includes an automated microtome for cutting serial sections from specimen blocks incorporated into the multi-foci microscope. The embodiment also includes a sequence of instructions for automated imaging and cutting of tissue block. The imaging parameters of the multi-foci multiphoton microscope can be characterized in terms of imaging speed and signal to noise ratio in two-dimensional (2D) specimens. In another embodiment, the imaging parameters of the multi-foci multiphoton microscope can be characterized in terms of imaging speed and signal to noise ratio in three-dimensional (3-D) samples. A preferred embodiment can be used, for example, to image tumor metastasis in a mouse model.

Two-photon microscopy (TPM) is a proven optical microscopy technique for imaging in highly scattering media and with a deep depth penetration of over 200 µm. TPM yields 3-D resolved microscopic images in deep tissues with minimal photodamage. In addition to providing tissue morphological information, two-photon spectroscopy based on autofluorescence also allows the monitoring of tissue metabolism and the identification of biochemical composition. Two-photon imaging and spectroscopy provide both structural and functional tissue information. Fluorophores can be excited by the simultaneous absorption of two photons each having half the energy needed for the excitation transaction. Since the two-photon excitation probability is significantly less than the one-photon probability, two-photon excitation occurs only at appreciable rates in regions of high temporal and spatial photon concentration. The high spatial concentration of photons can be achieved by focusing the laser beam with a high numerical aperture objective to a diffraction-limited spot. The high temporal concentration of photons is made possible by the availability of high peak power mode-locked lasers.

TPM allows 3-D biological structures to be imaged with resolution comparable to that found in confocal microscopy but with a number of significant advantages. Conventional confocal techniques obtain 3-D resolution by using a detection pinhole to reject out of focal plane fluorescence. In contrast, two-photon excitation achieves a similar effect by limiting the excitation region to a sub-micron volume at the focal point. This capability of limiting the region of excitation instead of the region of detection is critical. Since out-of-plane chromophores are not excited, photobleaching and photo-damage of biological specimens is restricted to the focal point. Further, two-photon excitation wavelengths are typically red-shifted to about twice the corresponding one-photon excitation wavelength. The significantly lower absorption and scattering coefficients at these longer wavelengths ensure deeper tissue penetration. In addition, the wide separation between the excitation and emission spectra ensures that the excitation light and the Raman scattering can be rejected without filtering out any of the fluorescence photons. This sensitivity enhancement improves the detection signal to background ratio.

Depth discrimination is an important feature of preferred embodiments of the present invention TPM. In TPM over 80% of the total fluorescence intensity comes from a 1 µm thick region about the focal point for objectives with numerical aperture of approximately 1.25. Thus, 3-D images can be constructed as in confocal microscopy, but without confocal pinholes. This depth discrimination effect of the two-photon excitation arises from the quadratic dependence of two-photon fluorescence intensity upon the excitation photon flux, which decreases rapidly away from the focal plane.

While TPM penetration depth of over 200 µm is superior to other high-resolution optical microscopy techniques, it may be insufficient to address a number of biological questions such as, for example, tumor metastasis in in-vivo models that have been shown to occur over great distances. A preferred embodiment incorporates a tissue sectioning device such as, for example, an automated microtome into a high throughput multi-focal multiphoton microscope to address the need to study specimens over distances. Alternate embodiments can include a rotating blade or vibratome to section tissue. By imaging serial sections 200-300 microns into a fixed tissue block, and then cutting off the top layer and imaging the newly exposed section, a preferred embodiment images through an entire fixed sample, and obtains high-resolution 3-D images of macroscopic volumes. In accordance with a preferred embodiment, the systems and methods of the present invention can be used by pharmaceutical companies, researchers, and clinicians interested in performing automated high-resolution image cytometry of thick samples.

A preferred embodiment of the present invention addresses a major difficulty of the slow imaging speed of typical two-photon microscopes that have frame rates between 0.5 to 10 s. Based on endogenous chromophore fluorescence, the typical time required for high-resolution imaging (500 optical sections) of a 200 µm thick skin tissue is approximately one hour. This long imaging time of the prior art is clearly impractical in the clinical setting. In addition, the slow data-acquisition rate also causes problems in image registration owing to the unavoidable motions of the subjects.

Different methods can be used to bring two-photon imaging speed to the video rate (approximately 30 frames/s). One method in accordance with a preferred embodiment uses line scanning. A line-scanning approach reduces image acquisition time by covering the image plane with a line instead of a point. The line focus is typically achieved with a cylindrical element in the execution beam path. The resulting fluorescent line image is acquired with a spatially resolved detector such as a charge coupled device (CCD) camera. The main drawback associated with line scanning is the inevitable degradation of the image point-spread function, especially in the axial direction. A second method, in accordance with another preferred embodiment which has been termed multiphoton multifocal microscopy (MMM), is analogous to Nipkow disk-based confocal systems. This method is based on a lenslet array that focuses the incident laser into multiple focus spots at the field aperture plane. The lenslet array is arranged similar to the traditional Nipkow design. Rotation of the lens causes the projected focal spots of the lenslet array to cover the field aperture plane uniformly. In another preferred embodiment, the MMM system uses raster scanning of a rectangular array of lenslets. A CCD camera is used to register the spatial distribution of the resultant fluorescent spots and to integrate them into a coherent image. The ability to image multiple sample regions simultaneously reduces total data-acquisition time. Resolution degradation is less in the case of multiple focal-spot scanning compared with line scanning. Multiple focal-spot scanning also has the advantage of being extremely robust.

A preferred embodiment of the present invention is optimized for high-speed, deep tissue imaging and uses a high-speed polygonal mirror. This method of a preferred embodiment is based on raster scanning of a single diffraction-limited spot. This embodiment includes a reflected light confocal microscope designed for deep tissue imaging. Since fluorescence is generated only at a single sample location at any given time, spatially resolved detection is not necessary. By replacing the CCD camera with a large, single-pixel detector such as a photomultiplier tube or an avalanche photodiode, the image resolution can be further improved by removing the dependence on the emission point-spread function. The spatial information is encoded by the timing of the raster scan pattern as in typical confocal microscopy. This is particularly important in turbid specimens such as tissues in which the scattered fluorescence signal is not confined in a single pixel of the CCD camera and degrades the image resolution. One embodiment of the system uses a CCD camera or CMOS imaging device. In another embodiment, a single-point detector can be implemented as a second channel in addition to the CCD camera to compare the two imaging modes in highly scattering specimens.

A preferred embodiment system includes a video-rate, two-photon scanning microscope based on a high-speed polygonal mirror scanner. This embodiment provides diffraction-limited resolution and is optimized for deep tissue imaging. Three-dimensional (3-D) cellular mitochondria distribution and the motion of protozoa, for example, have been analyzed using this system.

Figure 1B:
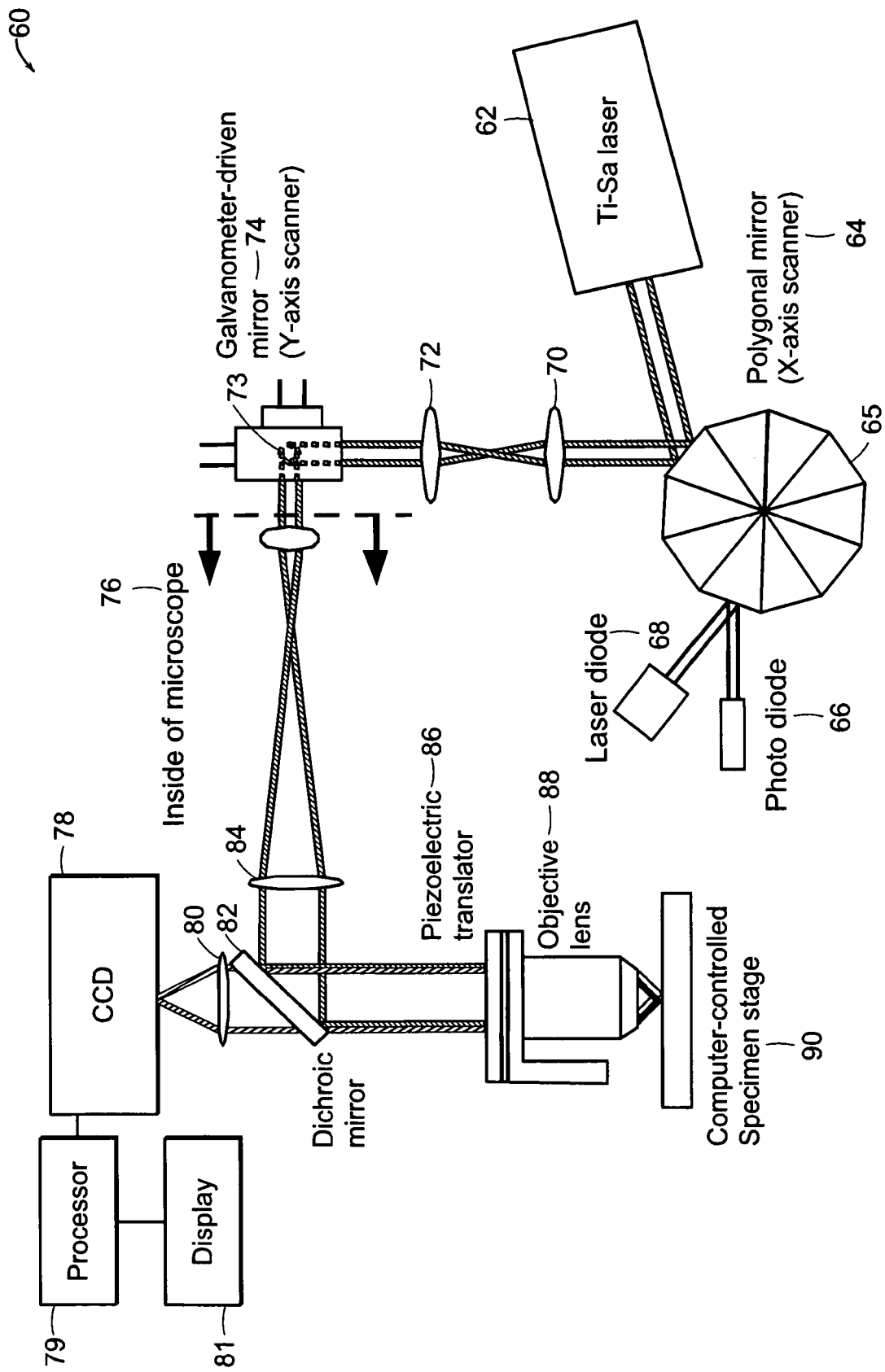

Schematics of a video-rate two-photon microscopy systems 10, 60 in accordance with preferred embodiments of the present invention are illustrated in FIGS. 1A and 1B, with a photomultiplier tube 30 and a CCD 78, respectively. A femtosecond titanium (Ti):Sapphire laser 12, 62, for example, Mira 900 supplied by, Coherent of Palo Alto, Calif. is used to induce two-photon fluorescence. The microscope system is optimized for the excitation wavelength in the range of preferably between 650 to 1200 nm. The laser beam is rapidly raster scanned across a sample plane by means of two different scanners. A fast rotating polygonal mirror 14, 64, for example, supplied by Lincoln Laser, of Phoenix, Ariz., accomplishes high-speed line scanning (x axis), and a slower galvanometer-driven scanner 26, 74 with 500-Hz bandwidth, for example, supplied by Cambridge Technology, of Watertown, Mass., correspondingly deflects the line-scanning beam along the sample's y axis. The spinning disc 15, 65 of the polygonal mirror is composed of 50 aluminum-coated facets (2 mm×2 mm) arranged contiguously around the perimeter of the disc. The facets repetitively deflect the laser beam over a specific angular range and correspondingly scan a line 50 times per revolution. Rotation speed is variable and different speeds, for example, of either 10,000, 15,000, 20,000 or 30,000 rpm can be selected. In the fastest mode, the corresponding scanning speed of 40 µs/line allows the acquisition of approximately one hundred 256×256 pixel images per second. The image acquisition rate in these embodiments is at least 100 times faster than conventional scanning systems.

Two lenses 22, 24, 70, 72 between the scanners function together as a relay element that projects the excitation beam deflected by the polygonal mirror onto a stationary point at the center of the y-axis scan mirror 25, 73. The microscope 28, 76 is placed such that its telecentric plane intersects with the stationary point at the y-axis scan mirror. The laser beam is coupled into an upright microscope such as, for example, Axioscope, supplied by Zeiss, of Thornwood, N.Y. by means of a modified epiluminescence light path. The beam is reflected by the dichroic mirror 34, 82 toward the objective and is focused on the specimen. To perform three-dimensional (3-D) volume scans, the objective 40, 88 is mounted on a computer-controlled piezoelectric objective translator 38, 86 with an approximate bandwidth of 1 kHz, such as, for example, a P-721.00, translator supplied by Physik Instrumente, of Waldbronn, Germany. The maximum z-axis travel range is approximately 90 µM. The maximum push/pull capacity is approximately 100/20N. It has a resolution on the nanometer scale with feedback control. Translation of the objective axially yields z stack of xy-plane images. The induced fluorescence signal is collected by the same objective and passes through the dichroic mirror. Residual scattered light is removed by an additional barrier filter, for example, a Schott BG39 filter, supplied by Chroma Technology, of Brattleboro, Vt. The fluorescence is recorded by an intensified, frame-transfer CCD camera 78 such as, Pentamax, supplied by Princeton Instrument, of Trenton, N.J. The 12-bit data of the 512×512 pixel CCD integrated circuit chip can be read out at a rate of 5 MHz. The maximum achievable image transfer rate is approximately 11 frames/s for 256×256 pixel images (2×2 pixel binning). The CCD frame rate that results in increasing frame speed of this system can be improved by use of a faster imager. Consequently, the polygonal mirror's spinning speed is adjusted to about 10,000 rpm, and the CCD exposure time is correspondingly set to approximately 90 ms.

Figure 2:
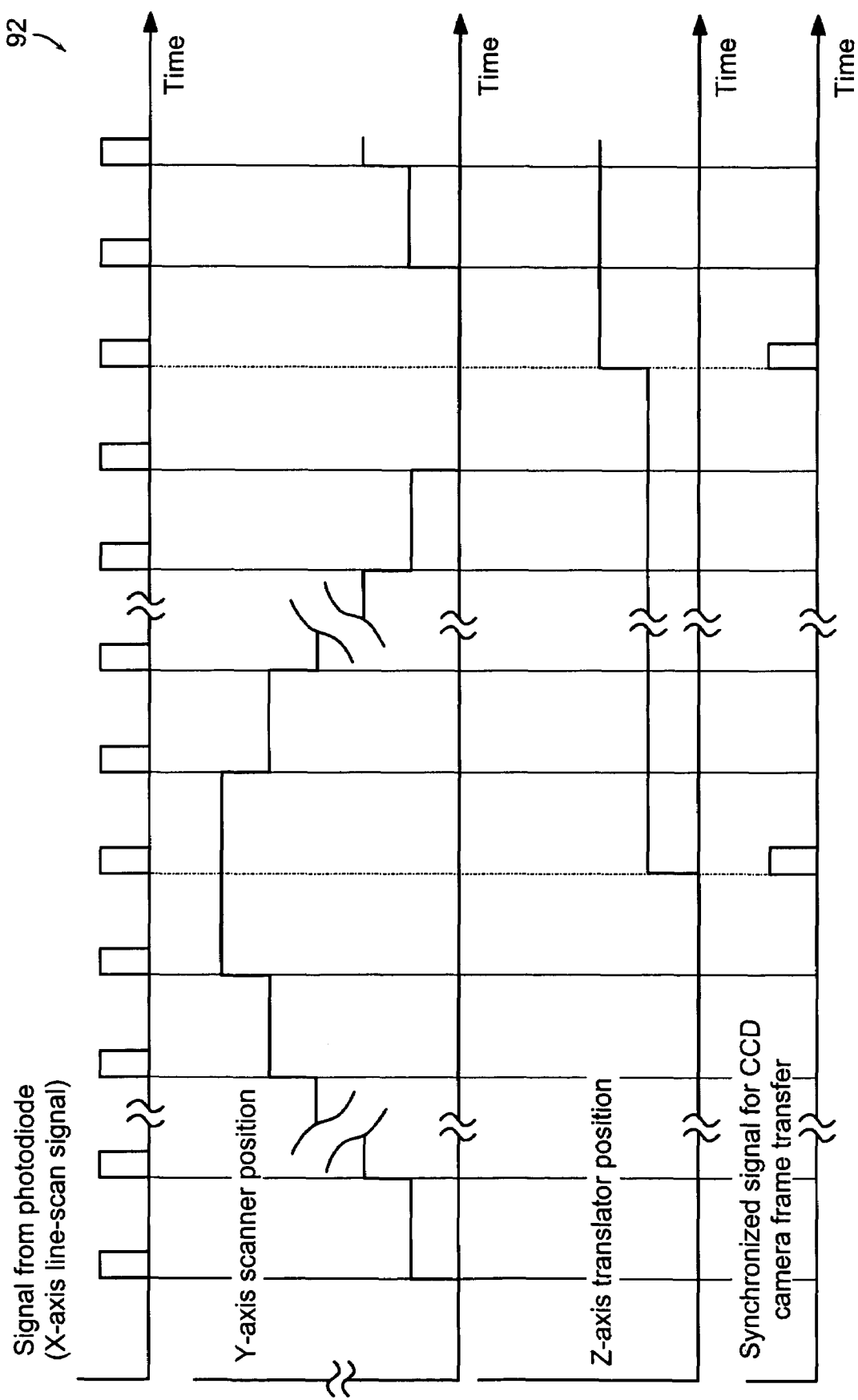
FIG. 2 is a timing diagram for the synchronization of actuators and sensors in accordance with a preferred embodiment of the present invention.

A separate laser diode 20, 68, for example, a 1 mW at 632 nm laser supplied by Thorlab, of Newton, N.J., along with a photodiode detector 16, 66 (Thorlab) is used to encode the polygonal mirror position and to generate a reference signal. This signal is used by a custom-built circuit board to synchronize the xy scanners, the objective translator, and the CCD camera as illustrated in the timing diagram illustrated in FIG. 2. The timing diagrams illustrate the synchronization of actuators and sensor. The signal from the photodiode is interpreted as an x-axis end-of-line signal. Y axis scanner changes its position synchronously with this end-of-line signal. After 256 lines are scanned (one plane having 256× 256 pixels), the z-axis piezoelectric objective translator steps to the next plane. The CCD camera also runs synchronously with the piezoelectric translator. The electronic circuit is based on reconfigurable logic, for example, XS4010E, supplied by Lilinx, of San Jose, Calif. that drastically enhances flexibility.

With respect to FIG. 1A, an eyepiece lens and a tube lens lead the beam to overfill on the back aperture of the objective lens. The beam is reflected by a dichroic mirror towards the objective, and is focused on the specimen. The induced fluorescence signal is collected by the same objective, passes through the dichroic mirror, and is collected at a highly sensitive photomultiplier tube, for example, R3896, supplied by Hamamatsu, of Bridgewater, N.J. A transimpedance amplifier, for example, C1053-51, also supplied by Hamamatsu, converts current output from the PMT to a voltage signal with amplification. The voltage signal is sampled with a 12 bit analog to digital converter, for example, AD9220EB, supplied by Analog Device, of Norwood, Mass., at approximately 11 MHz and is transferred to the custom-made interface card. The sampling rate is chosen to ensure all the signals from the incoming photons are sampled by sampling faster than the bandwidth (5 MHz) of the transimpedance amplifier. The interface card generates the signal for each pixel by accumulating the digital signals during the pixel resident time, for example, 720 nsec and transfers it to a computer. Although this analog detection method is lower in signal to noise ratio than single photon counting, it is suitable for 3-D cytometry where the fast imaging speed demands the use of high laser power that results in a non-negligible probability that multiple photons may arrive simultaneously at the detector. A separate laser diode (1 mW @632 nm, supplied by Thorlab, of Newton, N.J.) along with a photodiode detector (also supplied by Thorlab, Newton, N.J.) is used to encode the polygonal mirror position and to generate a reference signal. This signal is used to synchronize the X, Y-scanners, the objective translator, and the PMT. A PCI-bus interface card for computer control is designed based on the reconfigurable-logic chip, for example, XCS30; supplied by Xilinx, of San Jose, Calif. It receives the reference signal and generates synchronous digital signals for actuation, acquisitions. It is composed of a PCI bus controller board, for example, S5933DK1, supplied by AMCC, of San Jose, Calif. and a custom-made piggyback board which has the reconfigurable-logic chip on it. Most of the digital circuit for scanner control and data acquisition is implemented in the reconfigurable-logic chip. Therefore, the addition and the modification of the functions of the interface card is very flexible and can be easily implemented.

Computer-controlled specimen stage, for example, H101, supplied by Prior Scientific, of Rockland, Mass. is used for the precise movement of sample in case of wide area imaging. It is driven by step motors in 3 axes and its resolution is ±3 µm. It is controlled from computer via the serial port. Its response time is approximately 0.5 sec, depending on the computer speed due to delay time from the computer and the travel distance. Significant improvement of this 3-D image cytometer is possible with a higher bandwidth stage. For the distinction of two fluorescent colors, two channel detectors can be set up with the combination of a dichroic mirror and two filters (long pass, short pass each). Long wavelength signal passes through the dichroic mirror and then are collected at the first channel PMT through the long pass filter. The signal with the short wavelength is reflected at the dichroic mirror, and then is collected at the second channel PMT through short pass filter. Current setup of filter set is for the discrimination of cyan and yellow fluorescent colors. A dichroic mirror, for example, 495DCXR, supplied by Chroma Technology, of Brattleboro, N.H. with cutting frequency 495 nm splits the fluorescent signal. A long pass filter (HQ500LP, Chroma Technology) with cut-off frequency at 500 nm passes only photons with longer wavelength. A short pass filter, for example, E490SP, supplied by Chroma Technology with cut-off frequency at 490 nm passes photons with shorter wavelength. Therefore, photons with longer wavelength that 500 nm pass through dichroic mirror and long pass filter and are collected at the PMT (channel 1). Photons with shorter wavelengths than 490 nm are reflected at the dichroic mirror and pass through short pass filter and are collected at the second PMT (channel 2).

It is instructive to estimate the maximum throughput rate of this system given the typical instrument and specimen constraints. Assuming the size of each cell is approximately 30 µm×30 µm and the size of imaging region in 200 µm×200 µm (256×256 pixels) with 25× objective lens, the number of cells captured in one frame image is in the range of 40-50. Extending this calculation to 3-D, since the two-photon microscope has a penetration depth on the order of a couple hundred micrometers in typical tissues, one can expect that 10 layers of cells can be imaged assuming cell thickness as 10-20 µm. If these cell layers are captured in 5 frames along the depth direction, the throughput rate of 3-D image cytometer is approximately 100 cells per second where the movement of specimen stage takes 0.5 seconds.

For a given 76-MHz pulse repetition rate of the Ti:Sappire laser, only approximately 12 pulses hit the sample during a typical pixel dwell time of 0.16 µs. It is important to optimize the light budget for both the excitation and the emission paths. Use of circular instead of linear polarized light, allows the average excitation power to be increased by approximately 40% without excitation saturation of the sample, which is essential for maintaining the diffraction-limited excitation point-spread function. The linear-polarized light of the Ti:Sapphire laser is circularly polarized by a quarter-wave plate, supplied by CVI Laser Inc. of Putnam, Conn. Next, both the deflection angle and the diameter of the scanning beam are balanced carefully to maximize the field of view and power throughout while still overfilling the objective's back aperture for diffraction-limited focusing. A number of objectives, for example, Fluar 100×, with a numerical aperture (NA) of 1.3, oil; Fluar 40×, NA 1.3, oil; Plan-Neofluar 25×, NA 0.8, water; Ziess are used and the corresponding line-scanning dimensions on the specimens are 45, 113, and 182 µm, respectively. Furthermore, these high-throughput objectives, along with a high-quantum-yield photodetector, allow the acquisition of approximately 5% of the total emitted fluorescence. Assuming a typical two-photon excitation volume of 0.1 fl and a fluorophore concentration of 10 µM, approximately 70 photons per pixel can be acquired in the fastest scanning mode (25-kHz line rate), which is sufficient to generate useful images. Typically, for chromophore saturation to be avoided, the average laser power incident upon the sample surfaces is less that 10 mW, and the excitation wavelength is in the range of 730 to 780 nm.

Figures 3A, 3B, 3C, 3D:
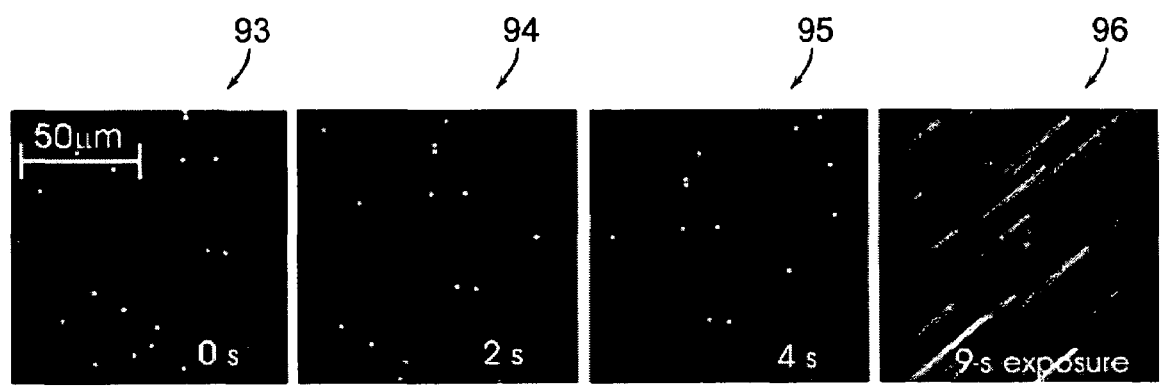
FIGS. 3A-3D are a time series of a 100 µm piezoinduced linear movement of 2 µm, yellow green spheres (movie of 100 frames) and an accumulative image of over the same time course as in FIG. 3A, respectively in accordance with a preferred embodiment of the present invention.

In an embodiment, to demonstrate real-time imaging with high spatial resolution, the piezo-driven linear displacement of a microscope slide that contained 2 µm-diameter, yellow-green latex spheres, for example, supplied by Molecular Probes, of Eugene, Oreg. immobilized in Fluoromount G supplied by Southern Biotechnology, of Birmingham, Ala. is stroboscopically recorded. The slide can be attached to a computer-controlled piezostage that is mounted such that the spheres are shifted diagonally across the microscope's xyimage plane at a rate of 10 μm/s. An image series containing 100 frames is acquired at 780 nm. Three selected frames spanning equal amounts of time are depicted in FIGS. 3A-3C. If these motions are imaged at a slower rate, only the trajectories of these spheres can be seen, but the individual spheres cannot be resolved. FIG. 3D illustrates this point with a single image acquired by exposure of the sample to the CCD continuously for 9 s.

Figures 4A, 4B:
FIGS. 4A and 4B are two-photon, three-dimensional resolved images of mitochondria distribution in mouse fibroblast cells as revealed with dihydrorhodamine labeling, with FIG. 4A illustrating a typical two-dimensional slice and FIG. 4B illustrating the three-dimensional reconstruction, respectively, in accordance with a preferred embodiment of the present invention.

In another example, to demonstrate the potential of 3-D cellular imaging, a z-axis series of images of mouse fibroblast cells, for example, CCL-92, supplied by ATCC, of Manassas, Va. is acquired that had grown to approximately three cell layers thick on a cover-glass chamber slide supplied by PGC, of Gaithersburg, Md. containing 1 ml of medium. The sample is labeled with dihydrorhodamine supplied by Molecular Probes, which is cell permeant and nonfluorescent. Dihydrorhodamine is first dissolved in dimethyl sulfoxide at a concentration of 10 mM. The stock probe solution is mixed with the medium in the chamber at a final concentration of 5 μM. With the presence of reactive-oxygen species within the cell, dihydrorhodamine is cleaved by reactive-oxygen species into individual fluorescent rhodamine molecules that localized in the mitochondria. One hundred images spanning a depth of 20 μm are acquired in 9 s with the excitation wavelength of 780 nm. The mitochondria distribution in the cell can be visualized clearly in 3-D as illustrated in FIGS. 4A and 4B. FIG. 4A is a two-photon, 3-D resolved image of the mitochondria distribution showing a typical two-dimensional slice, while FIG. 4B shows the 3-D reconstruction. With successive scanning, the fluorescence intensity is observed to increase consistently with photoinduced production of reactive-oxygen species in cells.

The reduction of photodamage is an important advantage of two-photon video-rate imaging as compared with traditional techniques, including wide-field fluorescence video microscopy and video-rate confocal microscopy. A preferred embodiment includes two-photon video-rate imaging with traditional wide-field fluorescence video microscopy to compare euglena locomotion. The imaging of euglena is based on their native chlorophyll fluorescence. A standard fluorescence microscope, for example, Leitz, supplied by Orthoplan2, of Stuttgart, Germany, equipped with a standard 100-W mercury arc lamp is used for wide-field fluorescence video microscopy. A three-color dichroic filter cube supplied by Chroma Technology, of Brattleboro, Vt. simultaneously provides excitation wavelengths at 350, 480, and 510 nm. The fluorescence images are acquired by a video-rate 3-chip color camera, for example, Sony, SXC-960MD. Time-lapse sequence images can be obtained in accordance with preferred embodiments which show the response of a euglena to the arc-lamp illumination, the euglena are observed to lose mobility almost instantly. The organism subsequently lost control of its cell shape within 3 s. The paralyzed euglena never regained activity after 10 s of data acquisition in a standard wide-field fluorescence microscope. In contrast, euglena motility can be noninvasively imaged by use of the two-photon video-rate microscope.

The incorporation of video-rate capacity is critical to be able to image large areas in a reasonable amount of time. FIG. 1B shows the schematic of a video rate system based on raster scanning of a single diffraction limited focal spot using a high-speed polygonal mirror. As described hereinbefore, a laser beam is rapidly raster-scanned across the sample plane by means of two different scanners. A fast rotating polygonal mirror accomplishes high-speed line-scanning (x-axis) and a slower galvanometer-driven scanner with a 500 Hz bandwith correspondingly deflects the line-scanning beam along the sample's y-axis. The spinning disc of the polygonal mirror is comprised of 50 aluminum-coated facets (2 mm$^2$), arranged contiguously around the perimeter of the disc. In the fastest mode, the corresponding scanning speed is 40 μs per line allowing the acquisition of approximately one hundred 256×256 pixel images per second. The image acquisition rate is 100 times faster than conventional scanning systems.

The laser beam enters the epiluminescence light path of an upright microscope. The beam is reflected by the dichroic mirror towards the objective, and is focused in the specimen. The induced fluorescence signal is collected by the same objective, and passes through the dichroic mirror. An additional barrier removes residual scattered light and a photomultiplier tube operating in analog mode records the signal fluorescence. In order to perform 3-D volume scans, the objective is mounted on a computer controlled piezoelectric objective translator with an approximate bandwith of 1 kHz. By translating the objective axially, z-stacks of xy-plane images are obtained. In order to be able to image samples whose physical dimensions extend beyond the field of view of the objective lens, a sample translation stage is incorporated into the system that can translate the sample macroscopic distances in the x/y plane. Thus, it is possible to image samples whose lateral dimensions are in the range of centimeters.

Figure 5:
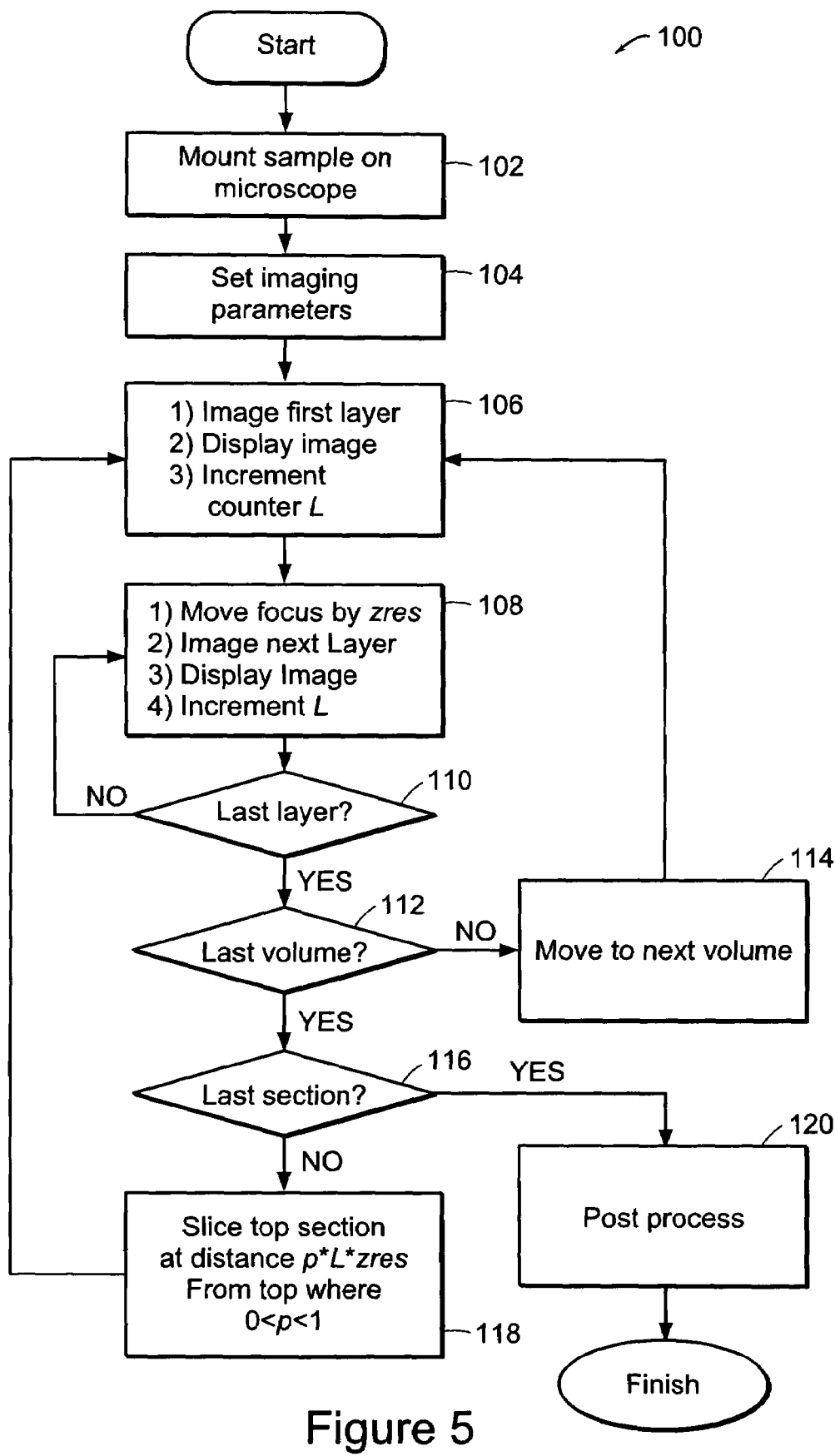
FIG. 5 is a flow chart of a method for volumetric scanning microscopy of a specimen in accordance with a preferred embodiment of the present invention.

FIG. 5 is a flowchart of the method 100 for volumetric scanning microscopy of a specimen in accordance with a preferred embodiment of the present invention. The method 100 begins with mounting the sample on the microscope per step 102. The sample is placed on a secure stage on the microscope. The stage has the ability to move a region of interest of the sample to different regions of the sample that lie outside the field of view of the objective of the microscope and move the sample towards a microtome for sectioning. The method then includes the step 104 of setting imaging parameters. The coordinate system that can be used is a Cartesian coordinate system with x and y in the object plane of the objective and z along the optical axis of the microscope.

A single section of the sample includes a series of volumetric images that are raster scanned by the macroscopic stage attached to the microscope. An individual volume block is specified by the number of x pixels by y pixels by z layers to be scanned. The x/y scan is performed by the fast scan optics (the polygonal and galvano scanner described hereinbefore) and the z scan is performed by a piezo actuator attached to the objective that physically translates the objective with respect to the sample in order to change the focus depth of the microscope. The actual physical separation between pixels is given by xres, yres, zres. Thus, an individual block has a physical dimension of (x*xres)*(y*yres)*(z*zres). The number of volume blocks that comprise an individual section are given by Xblocks and Yblocks.

An overlap connecting images can also be specified both in the x and y directions and the z direction. It is necessary to overlap the images so one can digitally reconstruct a macroscopic image in the computer by having the computer register the images. The cutting depth of the microtome can also be specified. This is less than the depth of the section that is imaged. In this way one can overlap successive sections. The number of sections is given by the parameter numSections.

Further imaging parameters that can be specified include, for example, but without limitation, intensity of the excitation source, scanning speed of the scanners, sensitivity of the detection electronics, and filter sets for the emission system.

The method 100 then includes the step 106 of imaging the first layer, displaying the image, and incrementing a counter L. The counter L is the current layer that is being imaged with an individual volume block. The image is displayed on the computer screen as it is acquired. After finishing the imaging of the current layer, the counter L is incremented. The method then includes the step 108 wherein the focus is moved by zres, and the next layer is imaged. Further, the image is displayed and the counter L is incremented. The piezo actuator focuses the objective deeper into the sample and images the next layers as previously described. The image is displayed and the counter L is incremented.

Per step 110 it is then determined if this is the last layer to be imaged in the volume block. If not, the method iterates or loops back to step 108 and repeats the procedure until the imaging of the volume block is finished.

The method 100 then includes the step of 112 which includes checking to see whether this was the last volume block to be imaged with the section. If not, the macroscopic stage moves the sample to the new location for next volume block per step 114. The macroscopic stage physically translates the sample with respect to the objective in the x/y plane and iterates the method by looping back to step 106.

The method further includes the determination of whether this is the last section to be imaged per step 116 if it had been determined that this was the last volume in step 112. If not, the method proceeds to the cutting step of 118 with the microtome. Step 118 includes slicing a top section at a distance of p*L*zres from top where 0<p<1. The sample is sectioned at a distance p*L*zres from the top of the sample. This distance is less than the depth that has just been imaged (L*zres). If it had been determined that this was the last section in step 116, then a post processing step 120 is entered. This step is described hereinafter.

For imaging large samples, a sectioning procedure can be automated and incorporated into the data acquisition process in accordance with a preferred embodiment of the present invention. Due to the extensive imaging time, all steps in the procedure can be automated. Thus, a microtome device is incorporated into the microscope.

A x/y/z scanner is used as the imaging translation stage. In one embodiment of the system, a motorized x/y scanner laterally scans the sample from each image section to the next. For 3-D imaging, the objective lens is driven with high accuracy by a piezo up to the penetration depth of the lens. Further, an axial translation can be incorporated into the microscope sample table. The z-axis, driven by a stepper motor, allows one to lift the sample up to a sharp microtome blade, which cuts off the previously imaged sample slice. The newly exposed sample section is then moved back under the objective lens by the y/x scanner.

Figure 6:
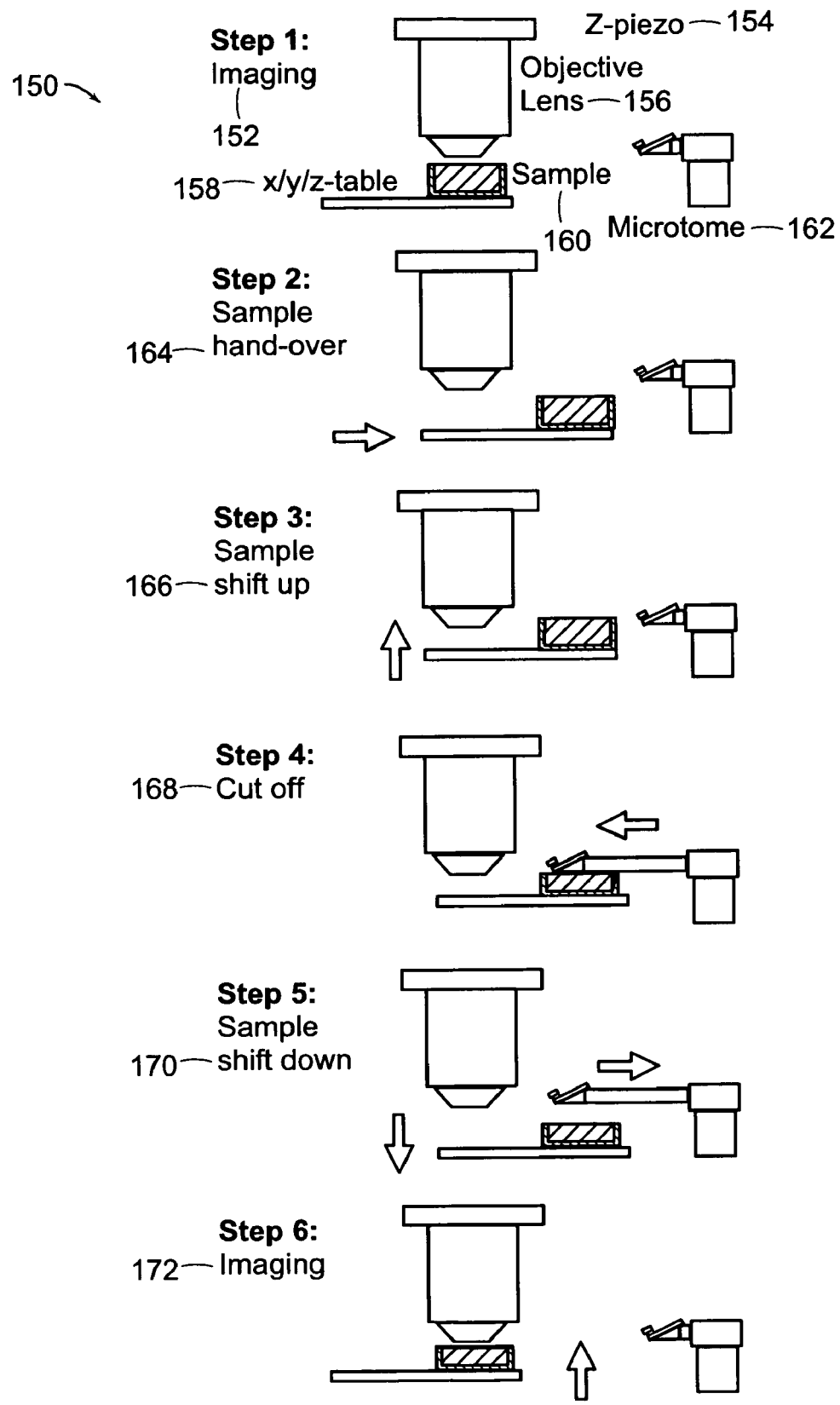
FIG. 6 is a diagram illustrating a procedure of an automated microtome for cutting serial sections from a sample block in accordance with a preferred embodiment of the present invention.

FIG. 6 is a diagram illustrating the procedure of an automated microtome for cutting serial sections from sample blocks in accordance with a preferred embodiment of the present invention. In step 1, imaging takes place down to the penetration depth of the lens (approximately 200 μm). The x/y scanner then drives the sample under the microtome. The z motor then elevates the sample up to the desired cut off mark in step 3. A second stepper motor moves a disposable blade over the sample in step 4, and cuts off the previously imaged region. In addition, in preferred embodiments, a sample disposal system is incorporated for the removed sample sections. In step 5 the sample is translated down again and moved back to the focal field of the objective lens (step 6). The cut-off point is slightly less than microscope penetration depth in order to allow some overlap between successive volumes. This is important for two reasons. First, a small overlap region allows re-registration of the imaged data volumes from different layers based on image correlation algorithms. Second, since the image planes are always below the cut plane, image distortion artifacts due to mechanical slicing of the specimen are minimized.

By specifying the approximate dimensions of the sample cube, the data processor or computer controls the automated imaging and slicing of the sample. The steps are repeated as before for every newly exposed region of interest.

Figure 7:
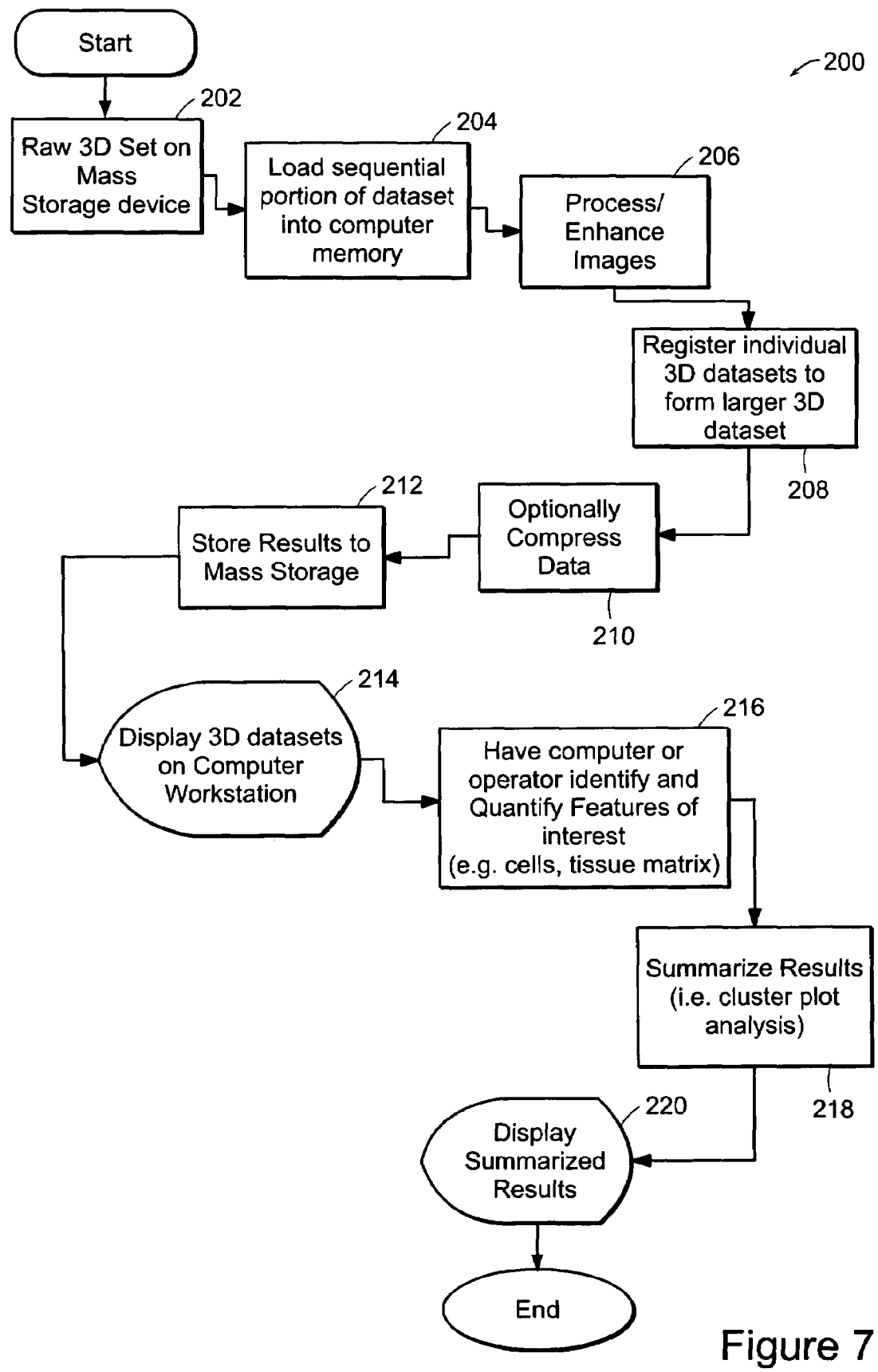
FIG. 7 illustrates a flow chart of the method for post processing the imaging data in accordance with a preferred embodiment of the present invention.
Figure 9B:
FIGS. 9A and 9B are high resolution volumetric images of a mouse brain in accordance with a preferred embodiment of the present invention.
Figure 9A:
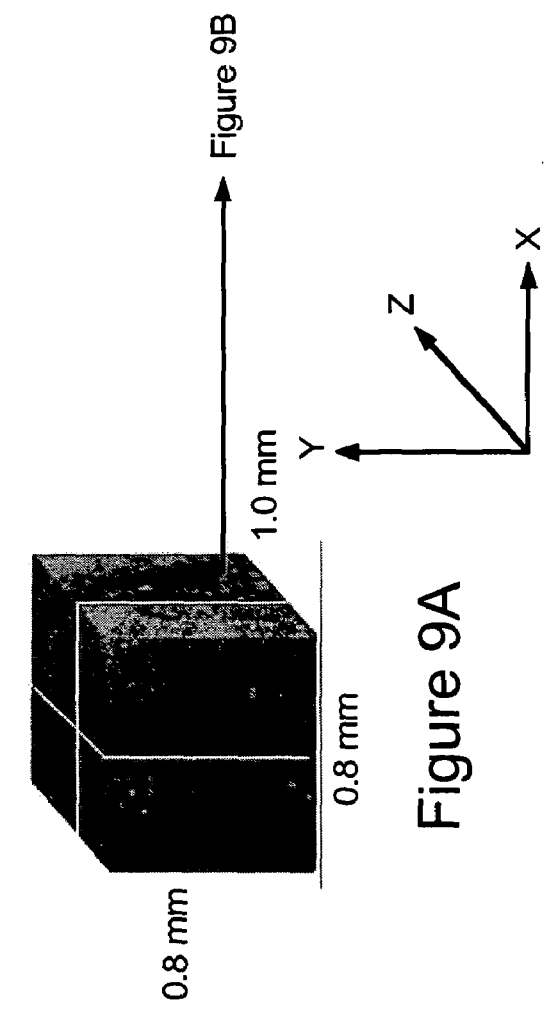

FIG. 7 is a flow chart illustrating the method of post-processing in accordance with a preferred embodiment of the present invention. The method begins with storing the raw three-dimensional (3D) data in a storage device per step 202. For example, the data storage requirements for a 1 cm$^3$ volume at a sampling resolution of 2 microns in all three directions may not exceed 300 GB. In this calculation a cube of 10 mm on a side is split into $1.25 \times 10^{11}$ detection volumes 2 μm on a side. If one assumes a 16 bit signal depth of, this leads to a storage capacity of 250 MB. As a consequence, the data can be easily stored on a commercially available hard drive.

An operating environment for the embodiments of the present invention includes a processing system with at least one high speed processing unit and a memory system. In accordance with the practices of persons skilled in the art of computer programming, the present invention is described with reference to acts and symbolic representations of operations or instructions that are performed by the processing system, unless indicated otherwise. Such acts and operations or instructions are sometimes referred to as being "computer-executed", or "processing unit executed."

It will be appreciated that the acts and symbolically represented operations or instructions include the manipulation of electrical signals by the processing unit. An electrical system with data bits causes a resulting transformation or reduction of the electrical signal representation, and the maintenance of data bits at memory locations in the memory system to thereby reconfigure or otherwise alter the processing unit's operation, as well as other processing of signals. The memory locations where data bits are maintained are physical locations that have particular electrical, magnetic, optical, or organic properties corresponding to the data bits.

The data bits may also be maintained on a computer readable medium including magnetic disks, optical disks, organic disks, and any other volatile or non-volatile mass storage system readable by the processing unit. The computer readable medium includes cooperating or interconnected computer readable media, which exist exclusively on the processing system or is distributed among multiple interconnected processing systems that may be local or remote to the processing system.

The method 200 then includes the step 204 of loading sequential portions of a dataset into a computer memory. The method then includes the step 206 of processing and enhancing the images. This step includes, for example, noise removal. For example, a median filter or gaussian filter is used to remove spurious noise from the images. Further, this step includes shading correction. The images are likely to be acquired under uneven illumination conditions. Intensity corrections based on either experimentally obtained reference test sample or theoretically derived intensity correction functions can be used to renormalize the 3-D dataset for an even intensity distribution throughout the sample.

The method further includes the step 208 of registration of individual 3-D datasets to form a larger 3-D dataset. Since the image of a macroscopic sample is obtained by acquiring multiple sub-images, it is necessary to reconstruct the entire image by combining or stitching together the sub-images. The process of properly aligning two overlapping images is known as the registration process. Given the large number of sub-images that must be taken to construct a single macroscopic image, this process is automated. An algorithm for accomplishing this is, for example, the normalized cross-correlation algorithm.

The next step includes the compression of the dataset per step 210 and can be optionally performed. Once the images have been processed, they can be compressed using either lossless or lossy compression algorithms. The JPEG standard can either employ lossless or lossy image compression. The level of compression used depends on the original quality of images and the subsequent analysis that can be performed. If a relatively low level of image detail is required higher compression settings can be used to obtain storage savings.

The method then proceeds to step 212 of storing the results to a mass storage device. The typical datasets that are acquired are in the range of 100 GB to 25 TB. Commercial hard drives that have capacity on the order of 250 GB can be purchased for very modest prices. It is straightforward to construct a RAID array of up to 8 drives which corresponds to 2 TB of data on a standard desktop computer. An index can be associated with dataset. This allows the division of a large image that has been processed and registered into a number of smaller images that can be spanned across several mass storage devices and easily loaded into a computer RAM memory on demand. This facilitates the display of the image by allowing the computer to quickly locate the region of interest for display.

The next step includes displaying the 3-D datasets on a computer workstation. A computer can be used to display the images. The user can specify the size and location of an image. The computer then loads the image of the mass storage device into the system memory. Algorithms for image sub-sampling can be used such that the entire image can be fit on the screen at once. Alternatively the user can pan through the image. FIGS. 8A-8C and 9A-9B illustrate, for example, some images and identify sub regions from large images that have been sub-sampled.

The method includes the step 216 wherein the computer or an operator identify features of interest. A major step includes the classification, or segmentation, of the 3-D image into various features. For a biological sample this can consist of the cells and extracellular material of the specimen.

There are a number of segmentation routines in use for 3-D images. The simplest approach is to use thresholding where the image is segmented into different components on the basis of the grayscale intensity at each pixel. Some other segmentation strategies include watershed, region-growing, and merge-split. Many of these necessitate the use of various image processing algorithms such as distance transforms, h-dome transformation, grayscale morphology operations (for example, but not limited to, opening, closing, erosion, and dilation). The particular segmentation strategy employed and image processing algorithms chosen depend on the nature of the specimen and quality of the image.

For fluorescent images, one can most likely make use of any spectral data contained with the images. The use of spectral data aids in the identification of key objects of interest, rather than just relying on the morphological information contained in a single grayscale image. The method 200 includes the step 218 of summarizing the results. Once the images have been segmented, it is necessary to tabulate the pertinent parameters for the objects. Parameters of interest may include, but are not limited to, the area of the region, perimeter, circularity, spectral composition, and texture. Cluster plot analysis can be used in a preferred embodiment.

Figure 10:
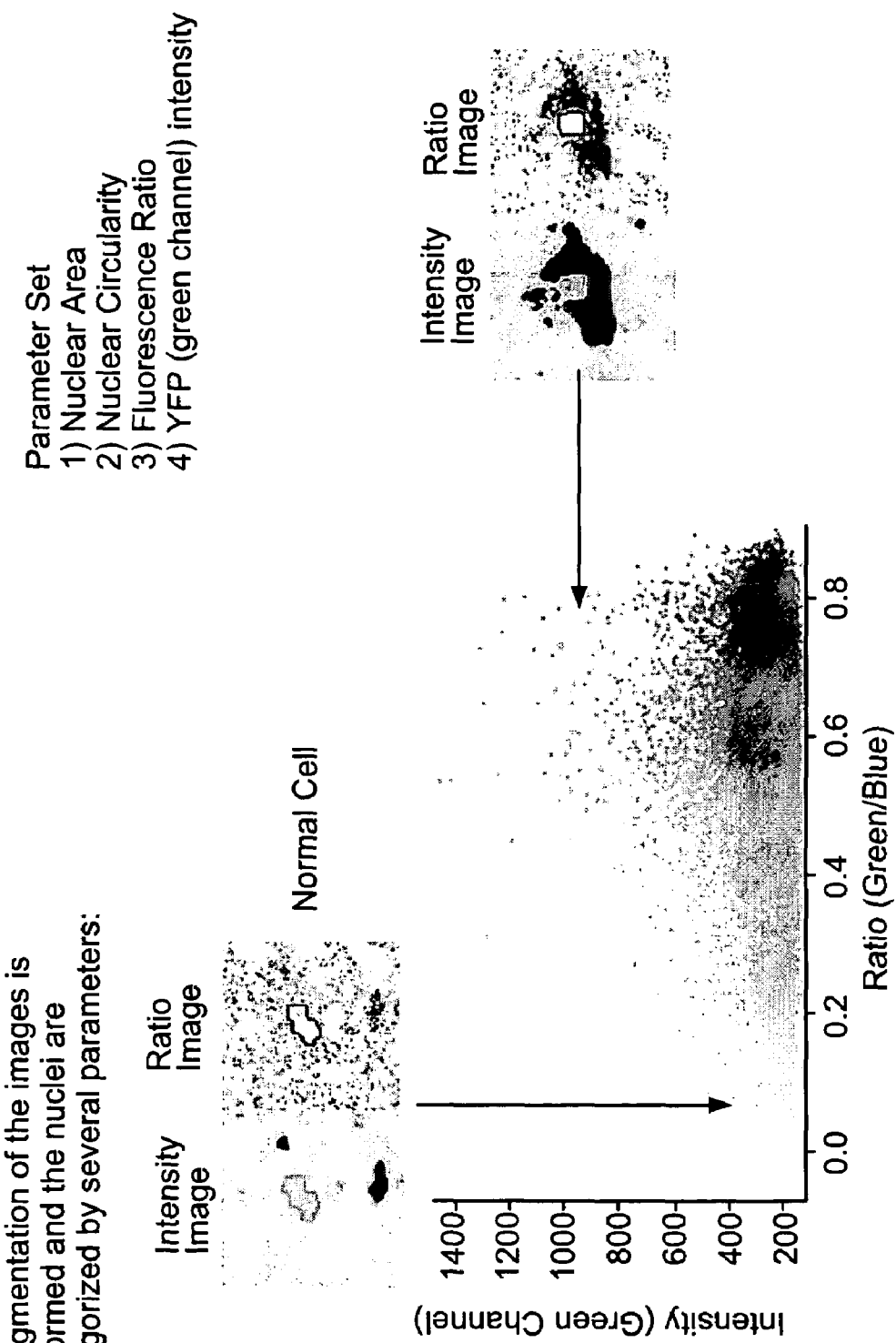
FIG. 10 graphically illustrates the results that are displayed by selecting a region of a multidimensional cluster plot of interest in accordance with a preferred embodiment of the present invention.
Figure 11A:
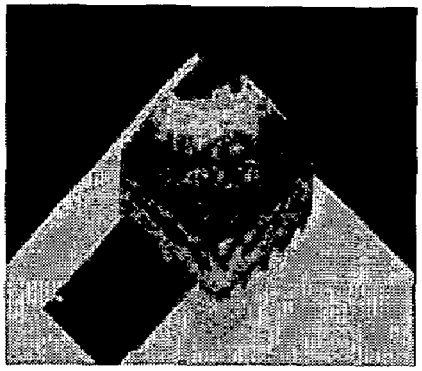
Figure 11B:
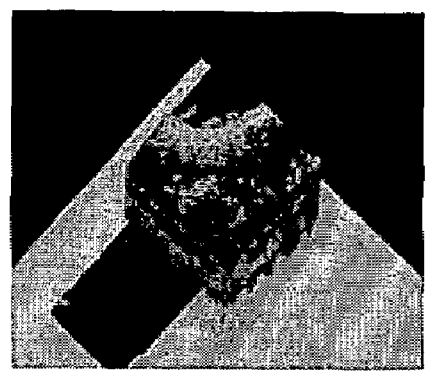
Figure 11C:
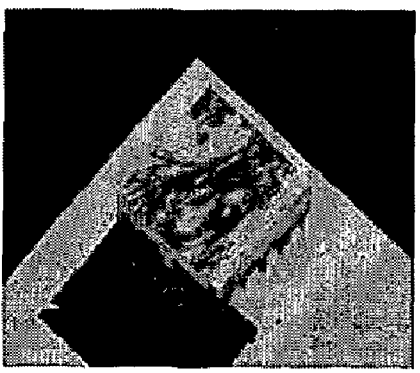
Figure 11D:
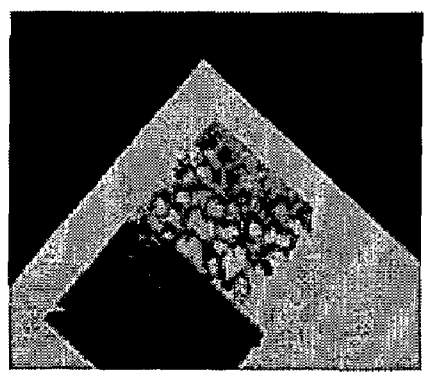
Figure 12A:
FIGS. 12A-12E illustrate images of collagen/elastin fibers in the dermis of frozen human skin acquired at successive depths of 80, 100, 120, 140 and 160 µm below the skin surface using two-photon video rate microscopy in accordance with a preferred embodiment of the present invention, wherein the size of each image is 80×100 µm$^2$.
Figure 12B:
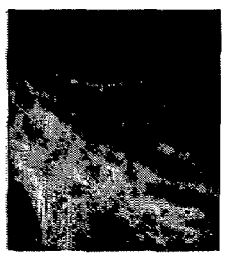
Figure 12C:
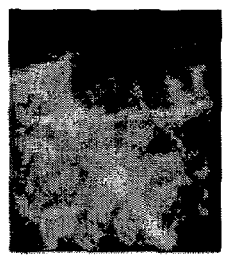
Figure 12D:
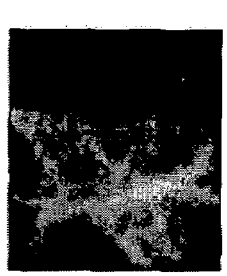
Figure 12E:
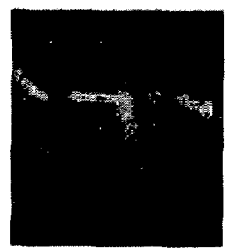

The method includes the step of 220 of displaying the results. There are a number of methods to display the results. A common method is to use what is known as cluster plots, which plot out the various tabulated parameters from the previous step along various axes. This allows an operator to identify quickly which objects have the specified parameters of interest by selecting the region of the multidimensional cluster plot of interest. FIG. 10 shows how a yellowish cell of biological interest can be located by selecting a point in the appropriate region in the cluster plot. The overall advantage of this approach is that the user does not have to manually inspect the entire image to find regions of interest.

To demonstrate the acquisition of deep tissue images using a video-rate two-photon microscope based on the polygonal mirror method, the collagen/elastin fiber structures in the dermal layer can be studied. One hundred images were taken at depths between 80 and 120 µm below the skin surface. The frame acquisition time was 90 ms and the whole stack was imaged with a data acquisition time of 9 seconds. The collagen/elastin fibers can be clearly observed.

The sampling rate of an embodiment of the 3-D image cytometer is approximately 4 $mm^2/20$ min with a 25× objective and a radial resolution of 0.72 µm apart. This corresponds to a processing rate of approximately 40 cells/second given the typical concentrations that is possible to plate on a coverslip. This processing rate depends on the choice of objective used and sample characteristics. To assess the instrument several tests were performed. Cell cultures containing a mixture of cells expressing cyan and yellow fluorescent proteins were prepared in concentrations ranging from 1/10 to $1/10^5$. The instrument was able to correctly identify the two subpopulations across the concentration ranges used. The instrument can also be used to identify rare recombination events in situ based on expression of enhanced green fluorescent protein (EGFP) or spectral variants of EGFP. A mouse has been engineered which contains two nonfunctional yellow fluorescent protein (EYFP) expression cassettes. Ordinarily, EYFP is not expressed since each EYFP cassette is nonfunctional; however, if a mitotic recombination event occurs at the right locus the EYFP expression system can become functional. This is a very low probability event with an occurrence on the order of $1/10^5$ to $1/10^6$, and hence the need for image cytometry. In preferred embodiments, the detection and analysis of recombination events in situ in intact tissue in mice that have been engineered with the EYFP expression system is performed.

This instrument has several advantages over other image cytometry systems. First, since two-photon excitation is being used, very low background levels are obtained due to both the separation of the excitation light from the emission light, and the lack of background fluorescence from out-of-focus planes. Another advantage is that due to the inherent 3-D section ability of the TPM, it is possible to use higher density of cells on the coverslip and still be able to resolve them from one another. This can be a limiting factor in other image cytometers since cells that overlap one another in the image plane will mask the signal from one another. Additionally, it is considerably easier to excite multiple chromophores than it is with one-photon excitation due to the broad two-photon excitation spectrum of many dyes.

In a preferred embodiment, the 3-D image cytometer can quantitatively measure cell fractions based on their fluorescence properties, using a mixture of two different fluorescent cells (expressing cyan and yellow fluorescent proteins). The cells can be studied at various ratios, ranging from 1/10 up to $1/10^6$. The embodiment of the system can find rare cells and identify subpopulations. Furthermore, the number of cells per second that the system can analyze can be established. The cells can be embedded into 3-D agarose blocks. This allows the system to test the slicing ability of the automated microtome in terms of being able to correctly register volumes after cutting into the sample.

Further, the ability of the instrument to image macroscopic biological tissue volumes can be demonstrated by investigating metastasis as sub-micron resolution in an entire mouse organ. The mouse model that can be used is the MetaMouse model from AntiCancer, Inc. AntiCancer, Inc., is a San Diego company that provides mice that have orthotopically implanted tumors. Metastasis of cancer cells from primary tumor cell is of major interest to cancer researchers. Surgical removal of cancerous tissue is often not successful due to the difficulty of removing all of the cancerous cells, some of which may have migrated to other regions due to micrometastes. Because the number of micrometastases can be very small their detection is often difficult and are thus of potential clinical significance.

In the MetaMouse model GFP labeled tumor cells are injected into a mouse. Firstly, one can image an entire mouse brain (1 cm$^3$) that has been injected with the GFP cells. The choice of organ is not critical. One can quantify the extent of micrometastases by removing and fixing the brain of the mouse and imaging it using the system of the preferred embodiment. This type of analysis can have potential commercial applications in the clinical setting with assays such as sentinel lymph node biopsy where there is interest in investigating the extent of micrometastases in cancer patients.

The preferred embodiments of the present invention can be used for fluorescence detection of genetic instability in mice. It is known that cancer is caused by the accumulation of mutations in oncogenes and tumor suppressor genes that control cell physiology and division. Since most people inherit two functional copies of each tumor suppressor gene, one allele from each parent, a mutation in one allele is generally inconsequential to a cell. However, should the remaining wild type copy become mutated in this heterozygous cell (referred to as loss of heterozygosity or LOH), the cell can become prone to tumorigenesis. Mitotic recombination has been estimated to be the underlying cause of LOH 25-50% of the time. In addition, mitotic recombination between misaligned sequences of the same chromosome can cause large deletions. Given that the mitotic recombination causes large deletions and also drives cancer-promoting LOH events, it is critical that one can learn more about the factors that modulate susceptibility to mitotic recombination.

Preferred embodiments of the present invention combine genetic engineering with mechanico-optical engineering to develop the technology to detect genetic instability in mammals. A transgenic mouse can be engineered to carry a fluorescent marker for identification of cells that have undergone a mitotic recombination event. A high-throughput two-photon microscope system makes it possible to quantify recombinant cells in situ in a variety of cells, to characterize the cell types most prone to mitotic recombination, and to discern the contribution of recombination events that occur in stem cells. Yet another important application is in studying the effects of cancer chemotherapeutics on mitotic recombination and in determining how specific genetic traits affect cellular susceptibility to chemotherapy-induced mitotic recombination. This line of research will ultimately aid in pharmacogenomics. This new tool will be of fundamental importance in revealing genetic and environmental processes that drive cancer-promoting mitotic recombination events in mammals. Thus, a system for rapid quantification of recombination events in mammalian cells can be developed which includes genetically engineering a substrate for detecting homologous recombination events in mammalian cells and determining the frequency of spontaneous recombination events in cultured mouse cells using the methods of imaging in accordance with preferred embodiments of the present invention described herein. Further, control transgenic mice can be created that constitutively express EGFP, which includes creating transgenic mice that carry the EGFP expression cassette in all cells and determining the strength of the EGFP signal for various tissue types.

In addition, in accordance with a preferred embodiment, mice have been developed to carry a recombination substrate that yields a fluorescent signal (EYFP expression) following mitotic homologous recombination. Furthermore, additional mice in accordance with another preferred development permit detection of recombination via expression of EGFP. These mice have a positive control counterpart that allows measurement of the potential signal strength following recombination. The spontaneous recombination frequency in both of these engineered mouse models is sufficiently high to allow detection using the methods of preferred embodiments of the present invention.

Preferred embodiments of the present invention, demonstrate the feasibility of high throughput two-photon screening for cells that have undergone recombination. This includes the use of the two-photon video-rate microscope for high throughput screening to demonstrate detection sensitivity of 1 fluorescent cell in $10^5$ wild type cells using cultured fibroblasts, and demonstrate the capacity of the two-photon microscopy system to map EGFP expression in mouse tissues using the transgenic mice developed.

Thus, the preferred embodiments provide the ability to identify fluorescent cells in mouse tissues with video-rate two-photon imaging.

As described hereinbefore, cancer is caused by genetic mutations that allow clonal expansion of increasingly aggressive cells. If there are no significant advances in cancer treatment and prevention, then we can expect that fully 25% of people alive today to die of cancer. Although recent progress has led to the identification of dozens of genes that promote tumorigenesis if they become mutated, we still know very little about those factors that cause genetic mutations in people in the first place. Understanding the causes of genetic change is at the core of understanding what makes people susceptible to cancer.

Tumor suppressor genes help prevent cells from becoming tumors. Normally, people inherit two functional copies of tumor suppressor genes, one allele from each parent. Loss of function of one tumor suppressor allele rarely results in any problems. However, if function of the remaining wild type allele is lost, that cell is at increased risk of developing into a tumor. While point mutations and deletions can promote both loss of function of the first and the second alleles, additional mechanisms can promote loss of function of a wild type allele if the cell already carries a mutant allele. Two such mechanisms are chromosome non-disjunction, which can cause complete loss of the chromosome that carries the remaining wild type allele, and mitotic recombination, which can cause the wild type allele to be completely replaced by the mutant version. In a heterozygous cell that carries one mutant and one wild type allele, loss of function of the remaining wild type allele is termed loss of heterozygosity (LOH).

There is now substantial evidence that mitotic recombination promotes tumorigenesis. In the case of colon cancer, up to 50% of all chromosomes have undergone LOH events. Mitotic recombination events are thought to be the cause of 25-50% of LOH events observed in tumors. Furthermore, two recently cloned tumor suppressor genes, BRCA1 and BRCA2, interact with components of the mitotic recombination machinery, providing further evidence that perturbations in the process of mitotic recombination can promote cancer. Despite its fundamental importance, we know very little about the genetic and environmental factors that modulate cellular susceptibility to homologous mitotic recombination in mammals, largely because of the dearth of effective model systems for studying these events in mammals in vivo.

DNA damage can disrupt the covalent structure of the DNA bases and trigger formation of single and double strand breaks (strand breaks can be caused directly by the damaging agent or they can result from enzyme interactions with base damage). Although the predominant form of double strand break repair is thought to be via direct end joining in mammalian cells, double strand breaks can also be repaired by homologous recombination. Homologous recombination has also been proposed to be important for repair of daughter strand gaps and reconstitution of broken replication forks, although the significance of these pathways in mammalian cells is not yet known.

Following S-phase, recombination between sister chromatids is an effective strategy for using the information in one chromatid to restore the other. Since the sequences in the sister chromatids are essentially identical, such recombination events should be undetectable. However, recombination between misaligned sequences of sister chromatids can cause deletions and recombination between homologous chromosomes can cause gene conversions. Thus, although mitotic homologous recombination is generally an effective repair strategy, a side effect of this strategy is that it can result in deleterious loss of genetic information.

By combining genetic engineering with opto-mechanical engineering and computer science, using the embodiments of the present invention volumetric tissue scanning microscopy system one can overcome the barriers that have, until now limited the detection of mitotic recombination events in tissue.

Thus, the system includes engineering mice that carry a genetic substrate that expresses either enhanced green fluorescence protein (EGFP) or enhanced yellow fluorescent protein (EYFP) if homologous recombination has occurred. In accordance with the present invention, mice have already been created that carry two non-functional EYFP expression cassettes in which recombination gives rise to EYFP expression. Cells have already been created that similarly allow detection of EGFP expression and these cells are being used to create transgenic mice. Recombination between the two non-functional mutant EYFP cassettes gives rise to fluorescence expression, and similarly recombination between two mutant EYFP expression cassettes gives rise to EYFP expression. A preferred embodiment of the present system uses these transgenic mice to detect recombination cells within tissues of animals. A plasmid containing two mutant EGFP expression cassettes can be created and transgenic mice can be created that carry copies of this construct in the genome of every cell. Recombination between the mutant EGFP sequences can restore gene function.

Even though it has already been demonstrated that expression of EGFP is readily detected in mouse skin and other tissues, it is critical that a preferred embodiment of the present system to detect these rare recombinant cells within intact mouse tissues. A two-photon microscope system that makes it possible to rapidly and automatically quantify rare fluorescent cells within thick tissue samples is used.

A major difficulty in the prior art in the application of a fluorescent marker for detecting mitotic recombination is the lack of imaging technology that can detect cells that have undergone a change in cellular fluorescence within intact tissues. Fluorescence confocal microscopy has traditionally been used to obtain 3-D structural information of tissues. However, the use of UV and blue/green excitation light in confocal microscopy restricts the maximum depth accessible in tissue to less than 30 µm. This depth restriction results from the high absorption coefficient of tissues in this wavelength range. Furthermore, fluorescence confocal microscopy also induces significant photodamage, which limits its use with living specimens. Chromophores can be excited by the simultaneous absorption of two-photons, each having half the energy needed for the excitation transition. Since the two-photon excitation probability is significantly less than the one-photon probability, appreciable two-photon excitation occurs only at a region of high temporal and spatial concentration of photons. A high spatial concentration of photons can be achieved by focusing the laser beam with a high numerical aperture objective to a diffraction limited location. The high temporal concentration of photons is made possible by the availability of high peak power mode-locked lasers. The two-photon cross section is typically on the order of $10^{-47}$ to $10^{-50}$ cm$^4$ sec$^{-1}$ photons$^{-1}$ molecules$^{-1}$.

Depth discrimination that arises from the quadratic dependence of two-photon fluorescence intensity upon the excitation photon flux is the most important feature of two-photon microscopy. For one-photon excitation in a spatially uniform fluorescent sample, equal fluorescence intensities are contributed from each z-section above and below the focal plane, assuming negligible excitation attenuation. This is a consequence of the conservation of energy. On the other hand, with the two-photon excitation over 80% of the total fluorescence intensity comes from a 1 µm thick region about the focal point for objectives with a numerical aperture of 1.25. For an excitation wavelength of 960 nm, the typical point spread function has a FWHM of 0.3 in the radial direction and 0.9 µm in the axial direction. Thus, 3-D images can be constructed as in confocal microscopy, but without confocal pinholes.

Two-photon excitation allows 3-D biological structures to be imaged with resolution comparable to confocal microscopes. However, for the imaging of thick tissues, with large absorption and scattering coefficients, it has a number of significant advantages. Firstly, the typical absorbency in the infrared spectral range is over an order of magnitude less than the near UV or the blue-green region. Using infrared excitation in the two-photon microscope minimizes the attenuation of the excitation signal. Secondly, there is reduced loss of infrared radiation due to scattering. In the simplest Raleigh scattering approximation, the scattering cross section decreases as the fourth power of the increasing wavelength. Thirdly, confocal microscopy uses the emission pinhole aperture to reject out-of-focus light. Inside deep tissue, scattering of the signal photons is inevitable. The consequent path deviation results in a significant loss of these photons at the confocal pinhole. The collection geometry for the fluorescence photons is less critical in the two-photon case, where a large area detector can be used without a pinhole aperture. Therefore, most of the forward scattered photons can be retained. Further, two-photon excitation minimizes tissue photo-damage. Conventional confocal techniques obtain 3-D resolution by limiting the observation volume. In contrast, two-photon excitation limits the region of photo-interaction to a sub-femtoliter volume at the focal point. This feature affords a major advantage, because fluorescence cells can be detected in living tissue over time, without incurring significant damage to that tissue.

The advantages of embodiments of the system in accordance with the present invention over existing systems for detecting recombination in mammals are numerous. Firstly, it is possible to quantify recombination events in numerous tissue types. Secondly, recombination events can be detectable in situ, allowing for analysis of the cell type that has undergone recombination. Thirdly, recombinant cells within thick sections can be visualized, making in situ data more informative and also facilitating analysis of a sufficient number of cells for robust statistical analysis using a small sample area. Fourthly, data collection can be rapid and automated, making experiments involving multiple exposure conditions and times highly feasible; and further, can be possible to monitor clonal expansion of recombinant cells over time, thus giving researchers valuable information about the susceptibility of stem cells to homologous recombination events.

The mice being developed for these studies can ultimately be crossed with other mice carrying a variety of engineered genetic defects. Thus, the influence of a myriad of genetic factors on the susceptibility of mammals to mitotic homologous recombination can be determined. Ultimately, this information will be invaluable in discerning the genetic factors that put some people at increased risk of getting cancer.

Ironically, DNA damaging agents are often used to treat cancer. Certain of these agents are known to promote mitotic recombination in cultured mammalian cells, and this may be an important factor in modulating patient susceptibility to secondary tumors. The proposed Recombo-Mouse system makes it possible to readily determine the recombinogenic effects of cancer chemotherapeutics. Furthermore, genetic factors that modulate susceptibility of animals to chemo-therapy-induced recombination can be identified. It is therefore hoped that the Recombo-Mouse mouse system will aid in the development of better anti-cancer drugs. In addition, understanding the genetic factors that modulate susceptibility of animals to the recombinogenic effects of cancer chemotherapeutics may ultimately facilitate optimization of cancer chemotherapeutic regimens to individual cancer patients.

There is a pressing need for improved methods for identifying agents in our food, environment, and pharmaceuticals that promote cancer. Animal models that are currently used to detect mutations in multiple tissue types are limited, in that only events that occur within a single gene are detectable; mitotic homologous recombination events are missed. Ultimately, by combining the Recombo-Mouse system with existing systems for detecting point mutations, it can be possible to determine the full range mutagenic effects induced by chemicals in our environment. The use of preferred embodiments of the two-photon microscopy system as the basis for developing a method for in situ detection of rare fluorescent cells within tissues is therefore important for the study of thick tissues, especially in the area of optical biopsy and tissue engineering. The ability to collect images deep within optically thick tissues in the fluorescent mode is unique to the two-photon approach.

Two-photon microscopic analysis has been successfully applied to a variety of system. These include non-invasive monitoring of embryo development, the study of calcium signaling deep within living brain slices, studies of the cornea, and studies of dermal tissues. The ability of this two-photon microscope instrument to resolve epidermal and dermal structures has been demonstrated by the imaging of mouse skin (FIGS. 11A-11D). A small sample of skin from a mouse ear was obtained two hours before the experiment and directly studied using the two-photon system; no special preparation procedures are required prior to imaging. Images were obtained at increasing depths, as show in FIG. 11C, allowing analysis of several cell layers. On the skin surface (far left), the cornified keratinocytes in the stratum corenum were observed. In the epidermal layer, individual keratinocytes can be clearly seen. Basal cells that have a smaller surface area can be visualized at the epidermal-dermal junction. Below the epidermis, collagen/elastin fibers in the dermis can be clearly resolved down to a depth of about 200 µm. Similar images have been obtained from human skin in vivo.

Because recombinant cells that express EGFP are rare, this embodiment requires high throughput imaging technology. Frame collection rates are typically between 0.5 to 10 seconds in prior art two-photon microscopes. High resolution 3-D imaging of tissue 100 µm deep in 3-D may take up to an hour, during which time about five hundred optical sections are acquired. This long imaging time is clearly too slow for this application. In addition, this slow rate of data acquisition would be incompatible within vivo studies, because of unavoidable movements of the tissue.

Incorporating video-rate imaging capacity is necessary to overcome these limitations. Video rate two-photon imaging methods can include line scanning or the simultaneous scanning of multiple excitation volumes. The nature of these methods dictates the use of an area detector, such as a CCD camera. Preferred embodiments of the present invention achieve high-speed two-photon imaging optimized for thick tissue studies, based on raster scanning of a single diffraction limited spot using a high-speed polygonal mirror. Since fluorescence is generated only at a single sample location at any given time, spatially resolved detection is not necessary. Therefore, either a CCD camera or a single pixel detector (such as a photomultiplier tube (PMT)) can be used for detection. A single pixel detector can improve image resolution by removing the dependence on the emission point spread function. This is particularly important in turbid specimens where the scattered fluorescence signal is not confined in a single pixel of the CCD camera, thus decreasing resolution. A large single point detector, such as a photomultiplier tube or an avalanche photodiode, can be used instead. The spatial information is encoded by the timing of the raster scan pattern, as in typical confocal microscopy. The embodiments have been described hereinbefore with respect to FIGS. 1A and 1B. By translating the objective axially, z-stacks of xy-plane images are obtained. The maximum z-travel range is in the range of 100-400 µm.

To demonstrate the acquisition of deep tissue images using a video-rate two-photon microscope based on the polygonal mirror approach, the dermal structures in ex vivo human skin were analyzed. The skin was previously frozen, but no other processing was prior to two-photon microscopy. The collagen/elastin fiber structures in the dermal layer were studied. One hundred images were taken at depths between 80 and 120 µm below the skin surface. The frame acquisition time was 90 ms and the whole stack was imaged with a data acquisition time of 9 seconds. The collagen/elastin fibers can be clearly observed. Representative images of the fiber structures are shown in FIGS. 12A-12E. These images demonstrate the advantages of video-rate two-photon microscopy.

In a preferred embodiment, control mice that carry the pCX-EGFP expression vector can be analyzed by two-photon microscopy to determine the strength of the fluorescence signal in various cell types. Recombination in skin and colon tissues can be initially analyzed. Thus, the fluorescence signal for all cell types within the skin and colon tissues of the pCX-EGFP mice can be evaluated. Founder mice will be crossed with C57B1/6J-Hfh11$^{nu}$ mice, that carry a recessive allele for the nude phenotype. By intercrossing F2 mice, mice that carry the pCX-EGFP vector can be identified by PCR. The nude transgenic mice may be amenable to analysis of EGFP expression in various cell types of the skin.

The detection of recombination events in tissue offers an exciting challenge in instrumental design. Preferred embodiments of the present invention identify mitotic recombination events in intact tissues such that cell type and proximity of other recombinant cells can be assayed. The ability to image a single cell and its biochemical state in thick, turbid tissue is provided. Preferred embodiments of the present invention detect EGFP fluorescence and reject the normal autofluorescence background of tissues.

At video-rate, the time required to collect 15,000 images is about 1.5 hours. To optimize the two-photon video-rate embodiment the excitation laser pulse train wavelength and temporal profile are manipulated to maximize two-photon excitation efficiency, minimize tissue autofluorescence, enhance image resolution, such as using PMTs and hybrid PMTs, to improve imaging speed and image signal to noise level. Secondly, the spectroscopic methods are implemented within the two-photon video-rate imaging system. This provides the necessary performance boost in this instrument. For example, incorporation of multiple color channels allows better separation of EGFP fluorescence from background autofluorescence. In addition, the implementation of confocal reflected light detection provides a non-fluorescent based method to image the normal cells. Thirdly, while the incorporation of automation and feedback control system is a common engineering practice, biomedical instruments with "intelligence" are rare. The need for an "intelligent" microscope is provided for this application and preferred embodiments. Given the mitotic recombination frequency of one cell in $10^5$, well over $10^6$ cells need to be imaged to obtain usable statistics. The acquisition of $10^6$ cells requires at least ten thousand images. It is clear that data acquisition by manual method is completely impractical. Thus, automations and "intelligent" algorithms are implemented in preferred embodiments to allow the microscope to decide the best imaging sequence. Furthermore, the amount of the data generated by this instrument is large. An intelligent instrument performs first-cut data processing and sorting.

A PMT detector in analog detection mode and a higher speed electronic interface circuitry based on PCI bus and reconfigurable logic are used in preferred embodiments to improve the speed of imaging. Second, for high throughput imaging of many cells, the ability to cover a larger area using more than a single field of the microscope is critical. Thus, an automated sample stage is implemented. A relatively low cost stage positioner manufactured by Prior, Inc. can be used. This stage positioner features a scanning range of 3 cm by 4 cm, which is sufficient to image nearly $10^6$ confluent cells growing on a cell culture dish. The position resolution/repeatability of the stage is relatively modest (0.5 µm). A relatively low-resolution stage is selected since there is a concern with counting and identifying individual cells, and the intracellular details are not critical. In an embodiment, the chosen stage can be controlled through a serial port communication. The control algorithm is integrated in the microscope of the preferred embodiment.

Alternate preferred embodiments include modifications to optimize the two-photon microscope system for high sensitivity imaging in tissues. Given the 76 MHz pulse repetition rate of the Ti:Sappire laser, only about 12 pulses hit the sample during a typical pixel dwell time of 0.16 µs. It is critical to optimize the light budget for both the excitation and emission light paths. For the excitation path, a circular instead of linear polarized laser light can be used. This may allow the use of higher average excitation power without excitation saturation of fluorophores, which causes resolution degradation of the image point spread function. Future improvement on the excitation efficiency consists of compressing the laser pulse width via group velocity compensation, increasing the pulse repetition rate, and finding the optimal excitation wavelength to maximize GFP excitation and minimize tissue autofluorescence. Further, a new detector technology, for example, hybri-photomultipliers, such as supplied by Delft Instrument may potentially provide substantial signal to noise improvement. These detectors have a high level of quantum efficiency. One important feature is that they can be operated in low noise single photon counting mode even when photons arrive in bunches. They can maintain this performance as long as there is less than 14 photons in each bunch.

To optimize sample stability, a tissue chamber can be created and the microscope stage can be cooled to 4° C. which may be necessary when data collection times are on the order of hours. A custom built sample chamber can be adapted for the automated microscope stage. The working area of the chamber can be 2.5 cm×2.5 cm. A microscope coverslip can be used at the bottom of the chamber to permit data collection from below, and a thicker glass plate can compress the skin against the coverslip. In the alternate preferred embodiment, the sample chamber may be cooled by circulating cold water through the upper glass plate and contact with the sample is prevented. To minimize problems with vibrations created by the cooling system, water can be circulated through the chamber housing.

Wavelength resolved spectroscopy can also be implemented. Spectroscopic measurements provide important additional information for the identification of tissue components. Wavelength resolved measurement can be efficiently implemented by directing emission light into multiple color channels using dichoric beam splitters and emission bandpass filters. A three-detector system covering wavelength ranges in blue, green, and red spectral regions can also be implemented. Emission resolved imaging allows better identification of EGFP expressing cells that have undergone recombination from tissue autofluorescence background. The fluorescence species primarily responsible for autofluorescence in tissues are the pyridine nucleotides with emission in the 400-500 nm and the much weaker flavoproteins from 450 to 500 nm. These broad band autofluorescence emissions can be preferentially rejected by spectrally separating them from EGFP fluorescence, which is centered at 510 nm and has a relatively narrow spectral width.

Further, preferred embodiments can include reflected light confocal imaging. Reflected light confocal microscopy has allowed real-time in vivo imaging of human skin and cornea in 3-D. Confocal microscopes can acquire clear structural images from these samples by excluding out-of-focus light. By confocally placing a spatial filter (pinhole) in front of a photodetector, only light emanating from the focal volume can pass through the pinhole. Out-of-focus illuminated objects form a defocused spot at the pinhole and correspondingly yields a weak signal. This optical sectioning effect allows imaging in 3-D. Confocal reflected light and two-photon fluorescence are complementary techniques that can allow different tissue structures to be visualized. Two-photon microscopes detect fluorescent structures in tissues, while confocal reflected light microscopes can image structures based on their refractive index differences. The ability of confocal reflected light imaging to acquire cellular structural information in the absence of fluorescence is particularly important for some embodiments of the present invention. The number and the distribution of normal cells that have not undergone mitotic recombination are important information. In principle, these cells can be imaged based on their endogenous pyridine nucleotides. However, due to the low quantum efficiency of these nucleotides, the imaging of these cells based on their cellular autofluorescence in intact tissues may be difficult. Instead, video-rate reflected light confocal imaging of different cell layers throughout the epidermis is very feasible.

Confocal reflected light capability can be easily incorporated into an existing two-photon microscope with no loss in detection sensitivity of the fluorescence signal. In typical two-photon microscope designs, the infrared photons reflected by the sample are rejected and lost at the diachronic mirror. An additional confocal detection path can be added to collect this reflected photons. The simultaneous imaging of human skin in both two-photon fluorescence and reflected light confocal modes has been demonstrated at 1 Hz frame rate as seen in FIGS. 12A-12E.

A preferred embodiment of the present invention includes a closed-loop biomedical microscope with full hardware automation and on-line image analysis and feedback control. Automation and closed-loop feedback control are two critical elements that have been lacking in biomedical instrumentation. Since the quantity of data acquired is extremely large (up to $10^{12}$ bytes per sample), instrument automation is critical for these high throughput analyses. The automation related tasks include: the incorporation of an automated sample stage (X-Y positioning) and piezo-driven objective positioner (Z-positioning). These devices will be synchronized with the polygonal and galvanometer-driven scanners and the detector circuits. It is important to note that automation is not sufficient. High throughput screening requires the instrument to be "intelligent". Given the complex 3-D tissue architecture, the microscope needs to recognize tissue physiology and position its next scan to acquire information from another cell layer. Thus, on-line data analysis systems to process the incoming data stream based on image segmentation and recognition as described hereinbefore are important. This allows the microscope to locate its scanning volume within the 3-D matrix of the tissue. A priori physiological information of a given tissue type may aid in this task. This on-line image analysis system is also used to perform the first level of data analysis. In many cases, it is possible to record only the images that contain fluorescent cells and discard other frames. This significantly reduces computer storage and data analysis requirements.

The system based on two-photon scanning microscopy has the inherent advantages of firstly, the ability of imaging thick tissue samples up to a few hundred micrometers, secondly, the ability to study tissue structures with subcellular resolution, thirdly, the ability to monitor tissue biochemistry and metabolism, and fourthly, the reduction of specimen photobleaching and photodamage. Therefore, 3-D image cytometer has the ability to characterize multiple cell layer specimens, in contrast with 2-D image cytometer where only single cell layer samples can be imaged. 3-D image cytometry in accordance with preferred embodiments of the present invention require high-speed two-photon imaging. Video-rate two-photon microscopy is achieved by adapting a polygonal mirror scanner and high-speed photomultiplier tubes as described hereinbefore. The frame rate is 13 frames per second in an embodiment. The throughput rate of this system is dependent on the choice of objective lenses, specimen properties, and the speed of computer-controlled specimen stage. A punched ear specimen from a transgenic mouse which carries green fluorescent protein has been imaged. The data demonstrate that this system can resolve a single green fluorescent cells in the tissue.

As a preliminary demonstration that 3-D image cytometer can quantitatively measure cell fractions based on their fluorescence properties, a mixture of two different fluorescent cells (expressing cyan and yellow fluorescent proteins) were studies at various mixing ratios ranging from 1/10 up to $1/10^5$. The goal of this experiment is to test whether the 3-D image cytometer can detect rare cells possessing fluorescent proteins of one color in the pool of the cells having different color fluorescent proteins. The ratio of $1/10^5$ is the same as the natural frequency of recombination events.

Yellow and cyan fluorescent proteins were chosen with the consideration that both colors can be simultaneously excited at single excitation wavelength and that the emission spectrums of two colors should be easily distinguishable. 3T3 mouse fibroblast cells were used as specimens for the experiment. Plasmids pCX Yellow and pCX Cyan consist of the coding regions for Enhanced Yellow Fluorescent protein (EYFP) and Enhanced Cyan Fluorescent protein (ECFP) from Clontech under the control of the pCX (chicken beta actin) promoter. 3T3 cells were lipfected with the Plasmids using LipofectAMINE-Plus (Gibco BRL). Samples were prepared on the glass slide.

Specimens with various mixture ratios from 1/10, $1/10^2$, $1/10^3$, $1/10^4$, and $1/10^5$ were imaged with 25× objective lens (Plan-Neofluar 25×, NA 0.8, Zeiss, Thornwood, N.Y.). In order to find enough rare cells to achieve reasonable statistical accuracy, we aim to detect at least 10 rare cells at each mixture ratio. Since these specimens are single cell layer samples, the throughput rate is much lower as compared to using this systems on multiple cell layer samples. However, the experiment is worthwhile in terms of testing system's ability of finding rare cells.

For this experiment, the excitation wavelength is set at 910 nm. For each image section, 10 layers of images were acquired. The fluorescence signal is recorded simultaneously with two channels for two color distinction. Fluorescent signal with wavelength longer than 500 nm are collected in the long pass channel (LPC) and one with wavelength shorter than 490 nm are collected in the short pass channel (SPC). FIG. 4A and FIG. 4B are the images from the LPC and the SPC. The mixture ratio of EYFP cells to ECFP ones is 1/10. Cells with both EYFP and ECFP appeared in the LPC. On the other hand, in the SPC, only cells with ECFP showed up. For the clearer distinction, ratio images were constructed by the combination of two images with a following formula.

$$PRATIO = \left(\frac{PLPass - PSPass}{PLPass + PSPass}\right)$$

Pratio represents pixel value of ratio images. PLPass and PSPass denote pixel values of LPC and SPC respectively. In order to remove noise, ratio images were masked with LPC images after noise of LPC images was reduced with thresholds. Pixel values of the ratio images are between −1 and +1. Cells with EYFP have pixel values in the range of 0.95, and the pixel values of cells with ECFP are in the range of 0.5. Specimens of other mixture ratios were imaged and the results were plotted. The x-axis is the expected ratio and the y-axis is the measured ratio and it shows linear relation between them.

As the last experiment, an ear punch biopsy specimen from a transgenic mouse was imaged. The mouse was engineered to carry enhanced green fluorescent protein (EGFP) gene. Different from the cell mixture which is one layer cell specimen, ear specimen is multiple layer sample and this experiment shown the capability of detecting fluorescent cells in the thick tissue. Wide are 3-D images were taken with 25× objective lens. 10×10 sections were imaged and the wide area images were reconstructed by stitching these sections together. The same channel setup as the one used in cell imaging was used.

For a parallel illumination, a "multiphoton microscopy" (MMM) can be used. This approach is based on using a custom fabricated multiple lens to focus the incident laser light into multiple foci at the field aperture plane. The multiple lenses are arranged in a pattern similar to the traditional Nipkow design. By translating the lens array it is possible to illuminate the field aperture plane. In existing MMM designs, a CCD camera is used as the detector. In contrast, preferred embodiment can implement a multi anode PMT, which provides greater sensitivity and higher signal to noise ratio.

Figure 13A:
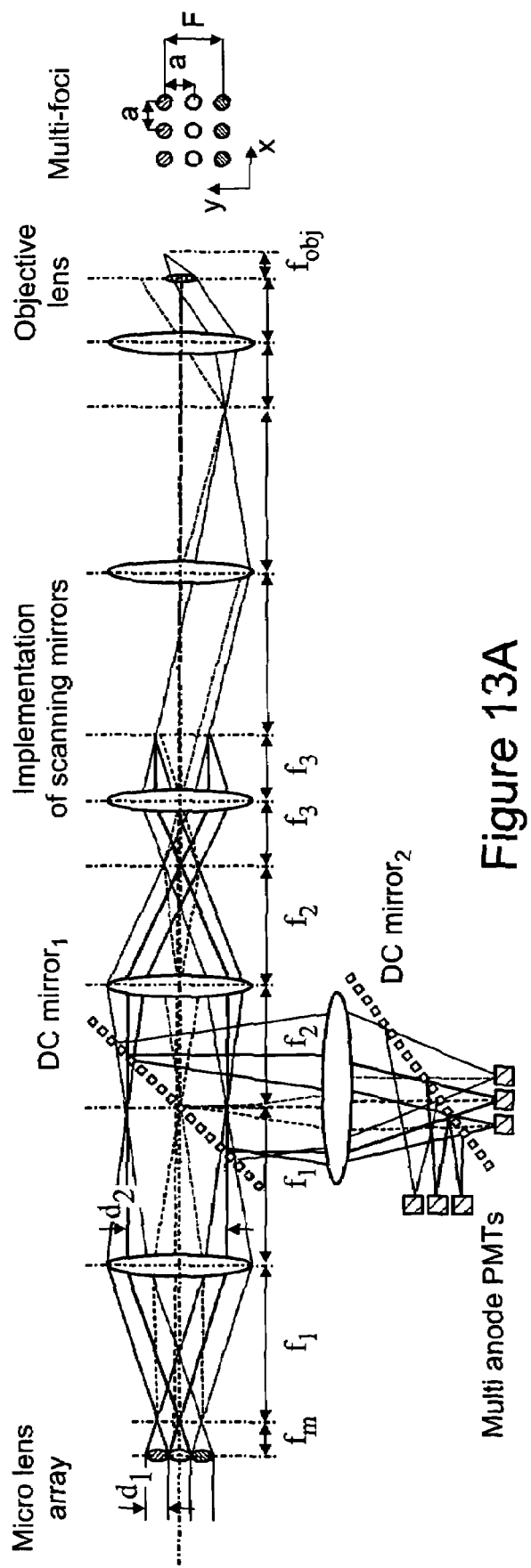
FIG. 13A is a diagram of a multifoci, multiphoton microscope (MMM) with two color detection, in accordance with a preferred embodiment of the present invention wherein multianode PMT is used as a detector for higher sensitivity.
Figure 13B:
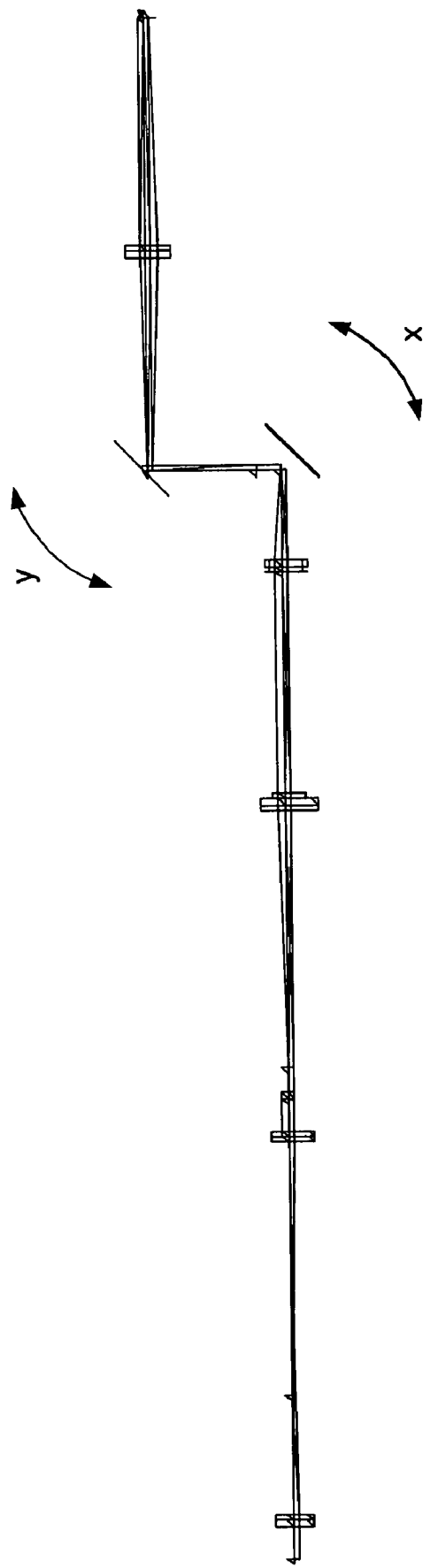
FIG. 13B is the Zemax simulation of the excitation beam path and FIG. 13C is the Huygens point spread functions of the foci, respectively.
Figure 13C:
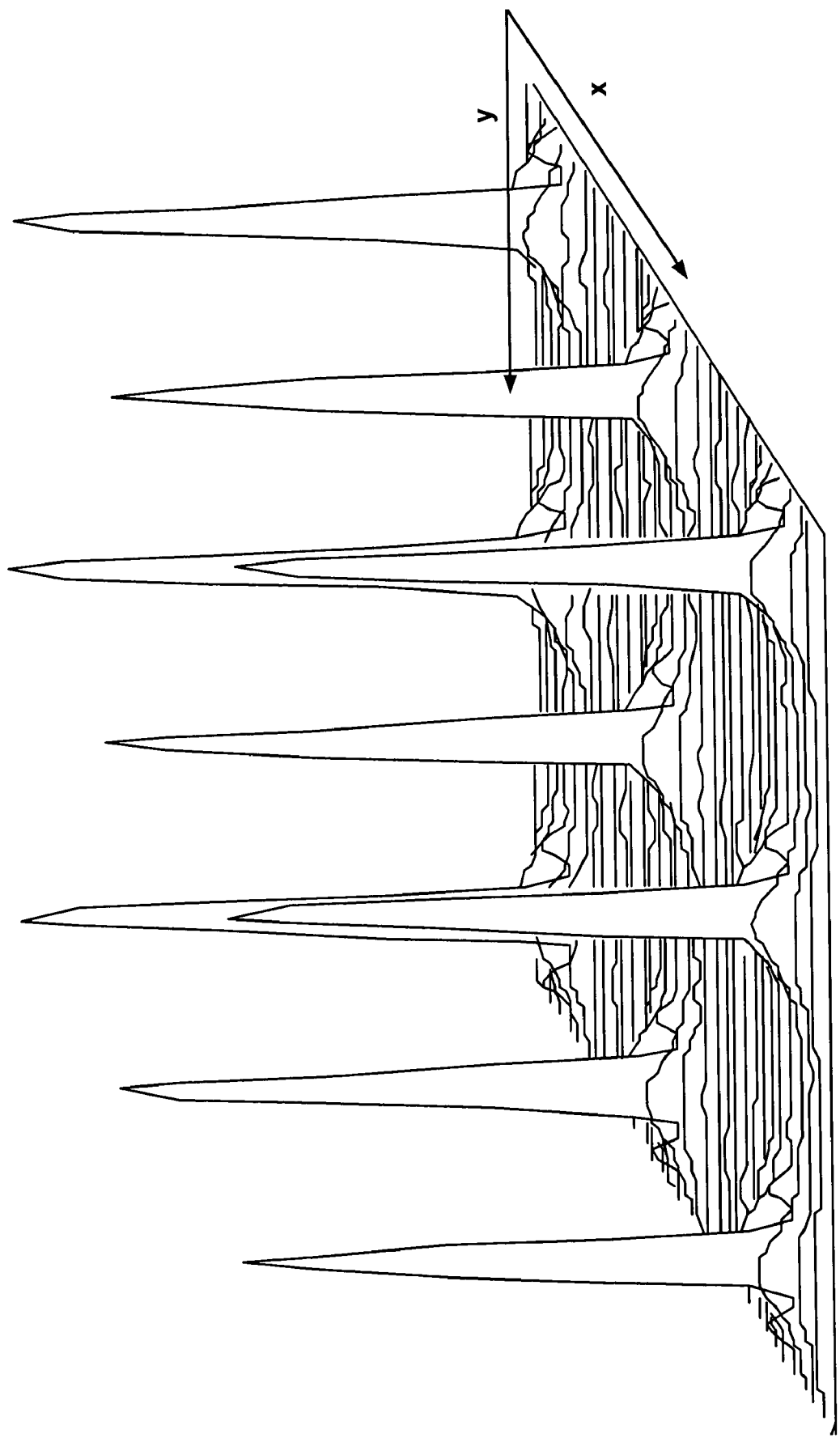
Figure 14A:
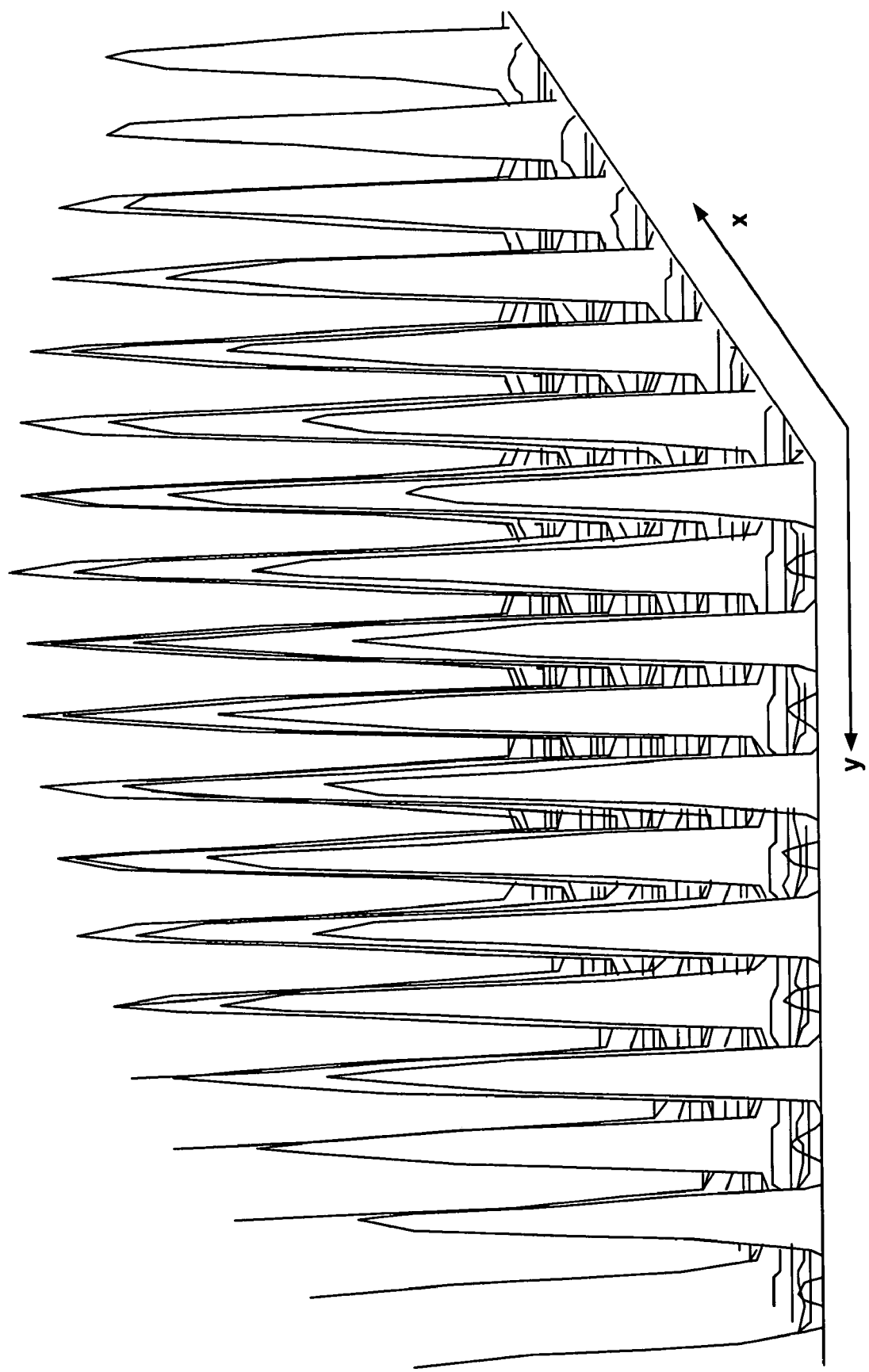
Figure 14B:
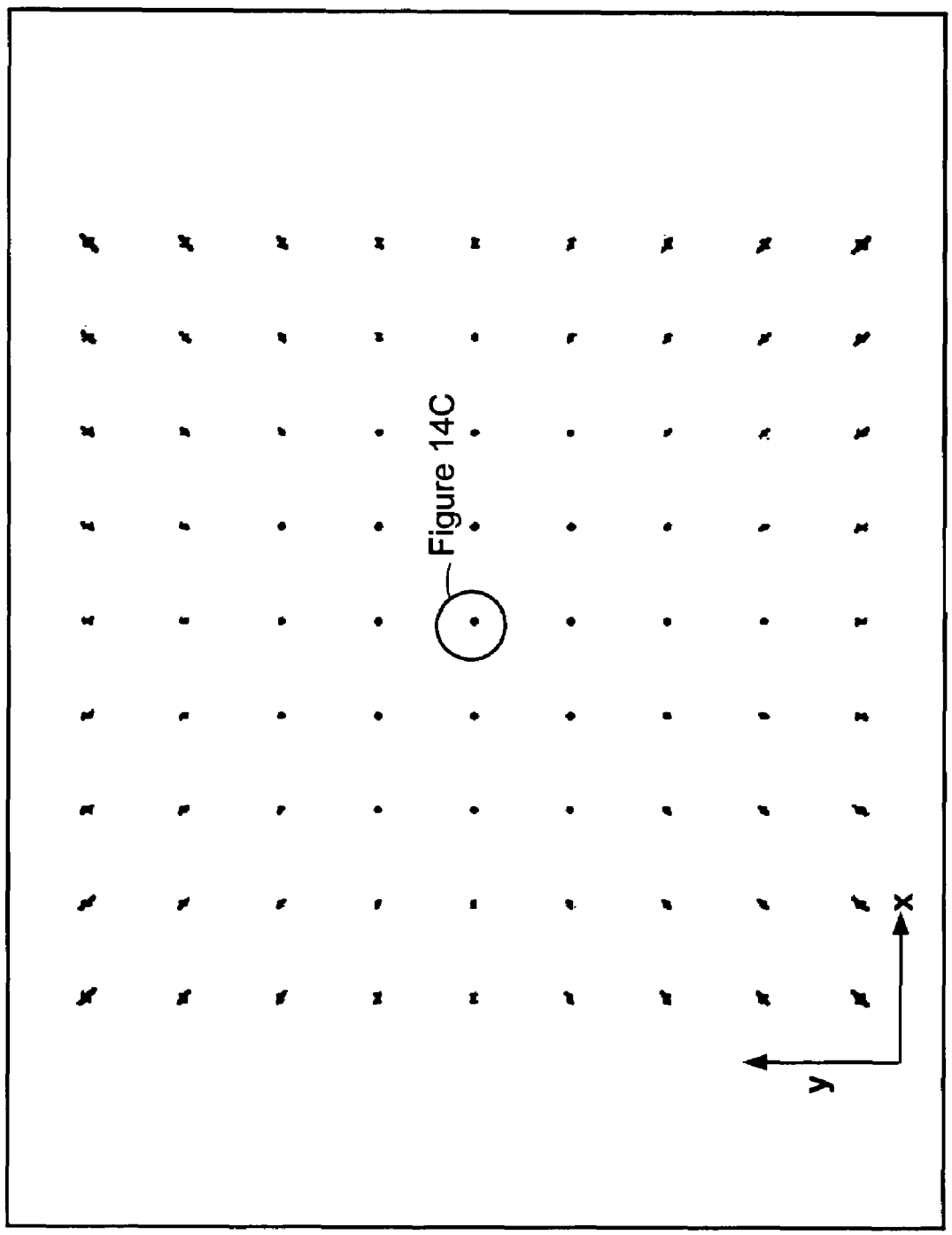
Figure 14C:
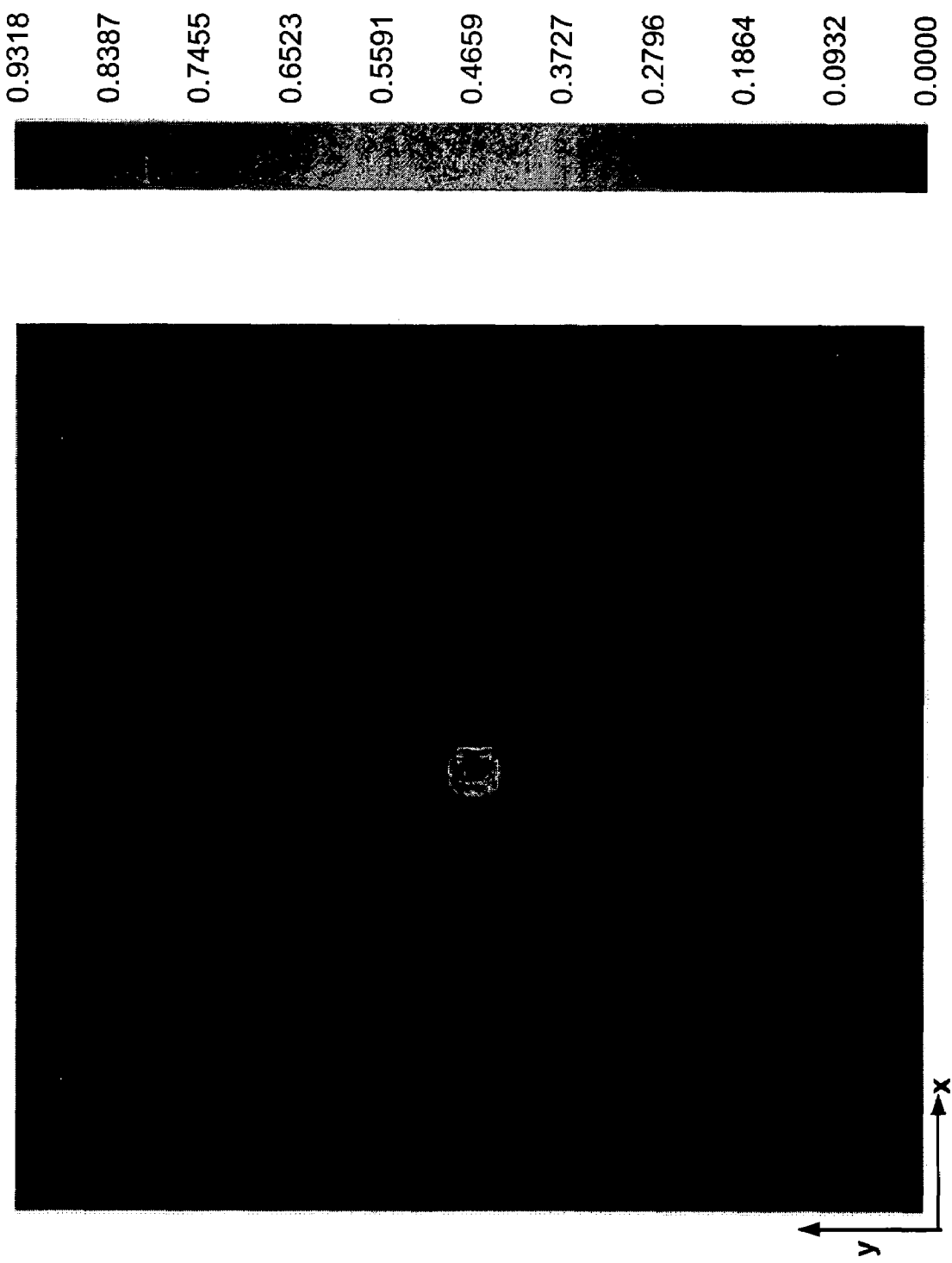

In the MMM design, an array of foci is generated at the field aperture plane. The emission from each focal point is guided over an optical pathway and again collimated by the excitation tube lens and is then directed to the objective. The collimated rays are designed to overlap at the back aperture of the objective and overfill it. The objective projects the individual focal points into the specimen. The scanning of the foci can be achieved by tilting two mirrors for the x and y direction, respectively (FIGS. 13A-13C). In FIGS. 13A-13C, the number of illustrated foci is reduced to 9 to simplify the illustration. The final setup incorporates an array of 8×8 lenses (FIGS. 14A-14C). In FIG. 13C, the Huygens PSF of the system is calculated. The emission light is collected by the objective in a epi-illumination mode and detected by the dichronic mirror into the detection unit and further focused by the emission tube lens. A multi anode PMT will be placed in each detection channel at the image plane.

A major limitation of all MMM's, currently designed is the need of a CCD camera as a detection device. The small pixels of the CCD camera behave as confocal pinholes and can cause smearing of the image due to the potential degradation of the emission point spread function light from the scattering inside turbid medium. More importantly, typical video rate CCD cameras are much nosier that PMTs, and do not have single photon sensitivity. Commercial video CCD cameras have a read noise on the order of hundreds to thousands of electrons and can be even worse when operated at the video rate. Even with high-end scientific grade video rate systems that use multiple read-out amplifiers, readout noises much lower than 10 electrons are rarely achieved. In contrast, PMTs offers an attractive alternative. Although PMTs have a quantum efficiency of about 30% (as compared to 80% for back-thinned, un-intensified CCDs), they have a gain of over $10^6$ and insignificant read noise. PMT detectors can routinely detect single photons.

Multi-anode PMTs have similar signal-to-noise characteristics to normal PMTs but also possess spatial resolution. Multi-anode PMTs typically contain 16 to 64 pixels, and are significantly lower in resolution than CCDs which may contain over 1 million pixels. However, this is not a real concern as the optimal number of detection elements only need to be equal to the number of foci generated. Position information can be encoded by both the detector pixel location (as in a traditional MMM system) and by the timing sequence of the raster scanning pattern (as in a single focal point scanning system).

In order to facilitate the identification of rare events and to better classify structures, we are introducing a second emission path into the MMM system to enable wavelength resolved spectroscopy, as is illustrated in FIGS. 13A-13C. To spectrally resolve samples labeled with multiple chromophores, a dichroic mirror can be incorporated into the emission path, which can spectrally separate the fluorescence onto two separate PMT arrays. It should be noted that it is important to design the emission path to eliminate as much out of focus stray light as possible. This can be achieved by constructing a pinhole matrix with pinholes large enough to prevent confocalization but small enough to minimize noise from stray light.

The electronics are designed to be used in parallel so that 64 channels can be accommodated by stacking four 16 channel detection electronics together. This is duplicated for each channel, so the entire system has a total of 128 PMTs.

The current laser system is capable of generating 1.8 W of mode-locked power at 480 nm and approximately 1.0 W at 920 nm. If it were possible to deliver all the power to the sample without any losses this in principle provides 28 mW and 15 mW, respectively, at the sample for each foci (with an 8×8 lenslet array). However, in a real-time system embodiment there is appreciable loss of laser power in the excitation optics. The system is expected to conservatively suffer a factor of four loss of excitation power before the sample, leaving approximately 7 mW and 4 mW at the sample depending on the wavelength. In order to maintain the same average power of 10 mW at each foci we would then need to account for a factor of 1.4 to 2.5 in additional power (for a factor 2 to 6.25 in signal intensity since intensity varies quadraticly with excitation intensity).

A method to maintain signal level is to implement a pulse compression system. In TPM the signal intensity linearly with the pulse width of the laser, so we can increase the signal intensity by employing a pulse compression system to pre-chirp the pulses before they reach the sample. With pulse compression it is possible to reduce the pulse width from its current value of approximately 400 fs to 100 fs. This gains a factor of four in expected signal increase. This is a sufficient signal for a 64 foci system at 840 nm excitation. The primary probe that is imaged at 920 nm and is green fluorescence protein (GFP). No significant difficulty is expected in imaging GFP, as it is a high quantum efficiency probe, and the autofluorescence levels of tissues are generally lower at longer wavelengths in TPM.

The MMM device has a frame rate of 30 Hz. Since it uses 64 times more foci, the pixel dwell time of 256 pix by 256 pix image is increased by a factor of ((10 Hz/30 Hz)×64) 20, leading to a pixel dwell time of 30 μs. Illuminating each foci with the same power as in the polygon approach, this leads to a 30 times brighter image.

It is important to estimate the image acquisition time for the system. In this estimate, the imaging time as well as the time required for the translation time required to move the sample to a new region needs to be considered. The field of view for a 0.9 NA air immersion lens (or 1.2 water immersion lens) is approximately 250 μm with a penetration depth on the order of 200 μm. This corresponds to an elementary volume element with dimensions of 0.25 mm by 0.25 mm by 0.20 mm, or 0.0125 mm$^3$. The imaging procedure is as follows: successive 2D planes deeper into the sample using the piezo on the microscope objective to move the objective with respect to the sample. The system is designed to take images of 256 pixel×256 pixel in a frame rate of 30 Hz, including the piezo scan in z direction.

The 0.9 NA objective lens creates a diffraction-limited spot of 0.5 μm×0.5 μm×1.0 μm in xy and z direction respectively. For large sample volumes, the imaging rate is improved by reducing resolution. We suggest a sampling resolution of 2 μm×2 μm×2 μm. An area of 128 pixel×128 pixel covers the lateral filed of the specified objective lens. As a result, the frame rate enhances to 120 Hz; four times its original value. An elementary image cube is then imaged in 0.83 s.

One can estimate the total time required the translation stage to move the sample. The existing stage translator is based on a stepper-motor based system and takes about 1 s to reposition. An area of 1 cm×1 cm with a depth of 200 μm can be split into 1525 volumes. The sample movement will consist of approximately 25 minutes. A small overlap in image volumes allows the elementary cells to be better registered and therefore extends the procedure to approximately half an hour. This is a considerable fraction of the imaging and we propose to improve the system performance by purchasing a new translation stage. Higher speed stage scanners based on servo-motors/air bearings are readily available and have a frequency response of over 10 Hz with a sub-micron precision. An optimized stage scanning system reduces the time to: 152 sec=2½ min. For the sample layer, the time for imaging, without accounting for movement, takes 1328 sec.=22 min. Therefore, the analysis of a sample layer of 200 μm thickness and a lateral extent to 10 mm×10 mm takes 1 hour total time at a resolution of 2 μm×2 μm×2 μm. With a faster stage scanner, the time can be easily cut down to approximately ½ hour.

As one goes deeper into the sample, the top layer is removed by an automated microtome. Each slicing procedure we account for 5 minutes. A 3-D sample of the extent of 1 cm×1 cm×1 cm contains a fifty 200 μm thick slices. Allowing an overlap of 10% between layers, 55 slicing procedures have to be taken until the whole cube is imaged. A total time of 4½ hours is allocated for the slicing. As a result, the total imaging time of the volume is about 60 hours [((55)×(1 hours+5 min)=3575 min=60 hours)].

In view of the wide variety of embodiments to which the principles of the present invention can be applied, it should be understood that the illustrated embodiments are exemplary only, and should not be taken as limiting the scope of the present invention. For example, the steps of the flow diagrams may be taken in sequences other than those described, and more or fewer elements may be used in the block diagrams. While various elements of the preferred embodiments have been described as being implemented in software, other embodiments in hardware or firmware implementations may alternatively be used, and vice-versa.

It will be apparent to those of ordinary skill in the art that methods involved in the system and method for determining and controlling contamination may be embodied in a computer program product that includes a computer usable medium. For example, such a computer usable medium can include a readable memory device, such as, a hard drive device, a CD-ROM, a DVD-ROM, or a computer diskette, having computer readable program code segments stored thereon. The computer readable medium can also include a communications or transmission medium, such as, a bus or a communications link, either optical, wired, or wireless having program code segments carried thereon as digital or analog data signals.

The claims should not be read as limited to the described order or elements unless stated to that effect. Therefore, all embodiments that come within the scope and spirit of the following claims and equivalents thereto are claimed as the invention.

What is claimed:

1. A method for imaging tissue, comprising the steps of:
   mounting the tissue on a computer controlled stage of a microscope;
   determining volumetric imaging parameters;
   directing at least two photon excitation light onto a region of interest;
   scanning the excitation light across a first portion of the tissue;
   imaging a plurality of layers of the tissue in a first volume of the tissue in the region of interest to provide first image data;
   sectioning the first portion of the tissue;
   scanning the excitation light across a second portion of the tissue;
   imaging a second plurality of layers of the tissue in a second volume of the tissue to provide second image data; and
   processing the first image data and the second image data to form a three-dimensional image of the tissue.

2. The method of claim 1, wherein the microscope comprises a multi-photon microscope.

3. The method of claim 2, wherein the excitation light has a penetration depth in the tissue of the range of approximately 200-500 μm.

4. The method of claim 1, further comprising detecting a fluorescent image.

5. The method of claim 1, wherein the image is a confocal reflectance image.

6. The method of claim 1, wherein the step of sectioning further comprises operating a microtome system that is integral with the microscope.

7. The method of claim 1, wherein the step of imaging a plurality of layers further comprises detecting at least 5 image frames per second.

8. The method of claim 1, wherein the step of scanning further comprises video rate scanning.

9. The method of claim 1, further comprising providing a depth resolution of approximately 0.1 to 2 μm.

10. The method of claim 1, wherein the step of scanning further comprises a low resolution mode and a high resolution mode.

11. The method of claim 1 wherein the sectioning step comprises moving the stage from an imaging position to a sectioning position, removing a layer of tissue with a sectioning tool, and moving the stage to the imaging position.

12. The method of claim 11 wherein the removing step further comprises cutting the layer of tissue with a blade.

13. The method of claim 11 wherein the moving step comprises translating the stage in an X-Y plane and elevating the stage to position the tissue relative to the sectioning tool.

14. The method of claim 1 further comprising performing a plurality of sectioning steps to remove successive layers of tissue.

15. The method of claim 1 further comprising programming a computer to control an imaging sequence and a stage translation sequence.

16. The method of claim 1 further comprising scanning the tissue using a moving mirror.

17. The method of claim 16 further comprising rotating a mirror relative to a light beam emitted by a laser.

18. The method of claim 16 further comprising scanning the tissue using a second mirror.

19. The method of claim 1 further comprising detecting images with an image sensor.

20. The method of claim 1 further comprising detecting images with a charge coupled device or CMOS imaging device.

21. The method of claim 1 further comprising detecting light with a photomuliplier tube detector.

22. A method of imaging tissue in-vivo, comprising the steps of:
   mounting the tissue in a multi-photon microscope;
   directing at least two photon excitation light onto a region of interest;
   scanning a plurality of layers of the tissue in the region of interest;
   imaging a plurality of layers in the tissue in the region of interest;
   detecting a fluorescence image of the region of interest in response to said excitation light; and
   processing the detected fluorescence image comprising the steps of:
   sequentially storing a plurality of three-dimensional image data sets;
   enhancing the image data sets;
   registering the plurality of three-dimensional data sets to generate a large three-dimensional data set; and
   displaying the three-dimensional data set of the region of interest.

23. The method of claim 22, wherein the step of processing further comprises compressing the three-dimensional data set.

24. The method of claim 22, wherein the step of processing further comprises identifying and quantifying features of the region of interest.

25. The method of claim 22, wherein the step of processing further comprises analyzing the three-dimensional data set.

26. The method of claim 22, wherein the step of imaging further comprises imaging mitotic recombination in the tissue.

27. The method of claim 22, wherein the step of scanning further comprises a low resolution mode and a high resolution mode.

* * * * *

UNITED STATES PATENT AND TRADEMARK OFFICE
CERTIFICATE OF CORRECTION

PATENT NO. : 7,372,985 B2
APPLICATION NO. : 10/642447
DATED : May 13, 2008
INVENTOR(S) : Peter So Page 1 of 1

It is certified that error appears in the above-identified patent and that said Letters Patent is hereby corrected as shown below:

Please delete the paragraph titled 'GOVERNMENT SUPPORT' encompassing Column 1, lines 7-9:

"This invention was supported, in whole or in part, by a grant R21/33CA84740 from the National Intitute of Health. The Government has certain rights in the invention."

and replace with:

--This invention was made with support under Grant No. R33 CA84740 awarded by the National Institutes of Health. The government has certain rights in this invention.--

Signed and Sealed this
Ninth Day of October, 2012

David J. Kappos
*Director of the United States Patent and Trademark Office*